(12) United States Patent
Miller et al.

(10) Patent No.: US 7,993,390 B2
(45) Date of Patent: *Aug. 9, 2011

(54) IMPLANTABLE OR INSERTABLE MEDICAL DEVICE RESISTANT TO MICROBIAL GROWTH AND BIOFILM FORMATION

(75) Inventors: Kathleen M. Miller, Shrewsbury, MA (US); Weenna Bucay-Couto, Burlington, MA (US); Jianmin Li, Lexington, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 953 days.

This patent is subject to a terminal disclaimer.

(21) Appl. No.: 10/789,398

(22) Filed: Feb. 27, 2004

(65) Prior Publication Data

US 2004/0249441 A1  Dec. 9, 2004

Related U.S. Application Data

(63) Continuation-in-part of application No. 10/071,840, filed on Feb. 8, 2002, now Pat. No. 6,887,270.

(51) Int. Cl.
*A61F 2/06* (2006.01)
(52) U.S. Cl. .................................... 623/1.44; 427/2.1
(58) Field of Classification Search ........ 623/1.42–1.48, 623/23.66, 23.7; 604/8; 427/2.1
See application file for complete search history.

(56) References Cited

U.S. PATENT DOCUMENTS

| | | | |
|---|---|---|---|
| 4,036,227 A | 7/1977 | Zaffaroni et al. | 424/428 |
| 4,054,139 A | 10/1977 | Crossley | 128/260 |
| 4,240,163 A | 12/1980 | Galin | 3/13 |
| 4,472,327 A | 9/1984 | Neefe | 264/1.9 |
| 4,603,152 A | 7/1986 | Laurin et al. | 604/265 |
| 4,723,950 A | 2/1988 | Lee | 604/322 |
| 4,731,080 A | 3/1988 | Galin | 623/6 |
| 4,853,978 A | 8/1989 | Stockum | 2/167 |
| 4,902,503 A | 2/1990 | Umemura et al. | 424/83 |
| 4,923,450 A | 5/1990 | Maeda et al. | 604/265 |

(Continued)

FOREIGN PATENT DOCUMENTS

DE  3347660 A1  7/1985

(Continued)

OTHER PUBLICATIONS

Swartz, R., et al., "Biofilm Formation on Peritoneal Catheters Does Not Require the Presence of Infection," *ASAIO Trans.*, vol. 37, No. 4, Oct.-Dec. 1991, pp. 626-634.

(Continued)

*Primary Examiner* — Suzette J Gherbi
(74) *Attorney, Agent, or Firm* — Mayer & Williams PC; David B. Bonham; Keum J. Park

(57) ABSTRACT

Disclosed are implantable or insertable medical devices that provide resistance to microbial growth on and in the environment of the device and resistance to microbial adhesion and biofilm formation on the device. In particular, the invention discloses implantable or insertable medical devices that comprise at least one biocompatible matrix polymer region, an antimicrobial agent for providing resistance to microbial growth and/or a microbial adhesion/biofilm synthesis inhibitor for inhibiting the attachment of microbes and the synthesis and accumulation of biofilm on the surface of the medical device. Also disclosed are methods of manufacturing such devices under conditions that substantially prevent preferential partitioning of any of said bioactive agents to a surface of the biocompatible matrix polymer and substantially prevent chemical modification of said bioactive agents.

32 Claims, 7 Drawing Sheets

U.S. PATENT DOCUMENTS

| | | | |
|---|---|---|---|
| 4,933,178 A | 6/1990 | Capelli | 424/78 |
| 4,946,899 A | 8/1990 | Kennedy et al. | 525/244 |
| 4,978,391 A | 12/1990 | Jones | 106/35 |
| 5,080,892 A | 1/1992 | Yamamori et al. | 424/78.09 |
| 5,091,205 A | 2/1992 | Fan | 427/2 |
| 5,091,442 A | 2/1992 | Milner | 523/122 |
| 5,098,379 A | 3/1992 | Conway et al. | 604/51 |
| 5,102,401 A | 4/1992 | Lambert et al. | 604/264 |
| 5,102,402 A | 4/1992 | Dror et al. | 604/265 |
| 5,130,159 A | 7/1992 | Shlenker et al. | 427/2 |
| 5,135,516 A | 8/1992 | Sahatjian et al. | 604/265 |
| 5,137,671 A | 8/1992 | Conway et al. | 264/130 |
| 5,165,952 A | 11/1992 | Solomon et al. | 427/2 |
| 5,171,318 A | 12/1992 | Gibson et al. | 623/5 |
| 5,176,665 A * | 1/1993 | Watanabe et al. | 604/317 |
| 5,178,870 A | 1/1993 | Schaeken et al. | 424/405 |
| 5,217,493 A | 6/1993 | Raad et al. | 623/11 |
| 5,261,896 A | 11/1993 | Conway et al. | 604/265 |
| 5,272,012 A | 12/1993 | Opolski | 428/423.1 |
| 5,279,594 A | 1/1994 | Jackson | 604/265 |
| 5,304,121 A | 4/1994 | Sahatjian | 604/53 |
| 5,328,698 A * | 7/1994 | Onwumere et al. | 424/486 |
| 5,328,954 A | 7/1994 | Sarangapani | 524/589 |
| 5,344,411 A | 9/1994 | Domb et al. | 604/265 |
| 5,360,415 A | 11/1994 | Yabushita et al. | 604/265 |
| 5,362,754 A | 11/1994 | Raad et al. | 514/566 |
| 5,366,505 A | 11/1994 | Farber | 623/11 |
| 5,370,681 A | 12/1994 | Herweck et al. | 623/1 |
| 5,389,314 A | 2/1995 | Wang | 264/25 |
| 5,409,012 A | 4/1995 | Sahatjian | 128/749 |
| 5,462,644 A | 10/1995 | Woodson | 204/131 |
| 5,468,787 A | 11/1995 | Braden et al. | 523/113 |
| 5,512,055 A | 4/1996 | Domb et al. | 604/265 |
| 5,569,463 A | 10/1996 | Helmus et al. | 424/426 |
| 5,599,298 A | 2/1997 | Sahatjian | 604/49 |
| 5,607,683 A | 3/1997 | Capelli | 424/405 |
| 5,611,354 A | 3/1997 | Alleyne | 128/846 |
| 5,616,119 A | 4/1997 | Davis | 604/19 |
| 5,624,704 A | 4/1997 | Darouiche et al. | 427/2.24 |
| 5,643,207 A | 7/1997 | Rise | 604/93 |
| 5,679,399 A | 10/1997 | Shlenker et al. | 427/2.3 |
| 5,693,034 A * | 12/1997 | Buscemi et al. | 604/265 |
| 5,707,366 A | 1/1998 | Solomon et al. | 604/265 |
| 5,716,406 A | 2/1998 | Farber | 623/11 |
| 5,741,331 A | 4/1998 | Pinchuk | 623/11 |
| 5,772,640 A | 6/1998 | Modak et al. | 604/265 |
| 5,853,745 A | 12/1998 | Darouiche | 424/423 |
| 5,902,283 A | 5/1999 | Darouiche et al. | 604/265 |
| 6,048,844 A * | 4/2000 | Falk et al. | 514/54 |
| 6,083,208 A | 7/2000 | Modak et al. | 604/265 |
| 6,096,070 A | 8/2000 | Ragheb et al. | |
| 6,106,505 A | 8/2000 | Modak et al. | 604/265 |
| 6,224,579 B1 | 5/2001 | Modak et al. | 604/265 |
| 6,261,271 B1 * | 7/2001 | Solomon et al. | 604/265 |
| 6,468,649 B1 * | 10/2002 | Zhong | 428/341 |
| 6,475,434 B1 | 11/2002 | Darouiche | 422/28 |
| 6,482,830 B1 | 11/2002 | Redkar et al. | 514/283 |
| 6,545,097 B2 | 4/2003 | Pinchuk et al. | 525/240 |
| 6,641,831 B1 | 11/2003 | Schierholz | 424/422 |
| 6,706,024 B2 | 3/2004 | Modak et al. | 604/265 |
| 6,719,991 B2 | 4/2004 | Darouiche et al. | 424/422 |
| 6,887,270 B2 * | 5/2005 | Miller et al. | 623/11.11 |
| 6,921,390 B2 * | 7/2005 | Bucay-Couto et al. | 604/265 |
| 6,929,705 B2 * | 8/2005 | Myers et al. | 148/243 |
| 2001/0010016 A1 | 7/2001 | Modak et al. | 623/1.42 |
| 2001/0022988 A1 | 9/2001 | Schwarz et al. | |
| 2002/0031601 A1 | 3/2002 | Darouiche et al. | 427/2.1 |
| 2002/0107330 A1 | 8/2002 | Pinchuk et al. | |
| 2003/0018306 A1 | 1/2003 | Bucay-Couto et al. | 604/265 |
| 2003/0024534 A1 | 2/2003 | Silvestri et al. | 128/846 |
| 2003/0078242 A1 | 4/2003 | Raad et al. | 514/150 |
| 2003/0153983 A1 | 8/2003 | Miller et al. | 623/23.7 |
| 2003/0199993 A1 | 10/2003 | Gellman et al. | 623/23.75 |
| 2003/0203991 A1 | 10/2003 | Schottman et al. | 523/334 |
| 2003/0224033 A1 | 12/2003 | Li et al. | 424/423 |
| 2004/0022824 A1* | 2/2004 | Li et al. | 424/423 |
| 2004/0166094 A1 | 8/2004 | Darouiche et al. | 424/93.4 |
| 2004/0166102 A1 | 8/2004 | Darouiche et al. | 424/93.45 |
| 2004/0208908 A1 | 10/2004 | Modak et al. | 424/423 |
| 2004/0249441 A1 | 12/2004 | Miller et al. | 623/1.15 |
| 2005/0161859 A1* | 7/2005 | Miller et al. | 264/209.1 |
| 2005/0255230 A1* | 11/2005 | Clerc et al. | 427/2.1 |
| 2005/0271698 A1* | 12/2005 | Bucay-Couto et al. | 424/423 |
| 2006/0264912 A1* | 11/2006 | McIntyre et al. | 604/891.1 |

FOREIGN PATENT DOCUMENTS

| | | |
|---|---|---|
| EP | 0 328 421 A2 | 8/1989 |
| EP | 0328421 A2 | 8/1989 |
| EP | 0 379 271 A2 | 7/1990 |
| EP | 0379271 A2 | 7/1990 |
| EP | 0970711 A2 | 1/2000 |
| JP | 01-121065 | 5/1889 |
| JP | 01-178540 | 7/1989 |
| JP | 04-500469 | 1/1992 |
| JP | 05-21960 | 3/1993 |
| JP | 08-117326 | 5/1996 |
| JP | 08-199002 | 8/1996 |
| JP | 10-024101 | 1/1998 |
| JP | 11-500330 | 1/1999 |
| JP | 2000-507842 | 6/2000 |
| WO | 90/02573 A1 | 3/1990 |
| WO | 93/10847 A1 | 6/1993 |
| WO | WO 93/10847 | 6/1993 |
| WO | 07-505131 | 6/1995 |
| WO | 96/22114 A1 | 7/1996 |
| WO | WO 97/14447 | 4/1997 |
| WO | 97/25085 A1 | 7/1997 |
| WO | 9836784 A1 | 8/1998 |
| WO | WO 99/47595 | 9/1999 |
| WO | 99/55396 | 11/1999 |
| WO | 0010622 A1 | 3/2000 |
| WO | 0032255 A1 | 6/2000 |
| WO | 00/57933 A1 | 10/2000 |
| WO | WO 01/03607 A2 | 1/2001 |
| WO | 0121229 A | 3/2001 |
| WO | WO 01/21229 A1 | 3/2001 |
| WO | WO 03/066119 A1 | 8/2003 |

OTHER PUBLICATIONS

Richards, G.K., et al., "Comparative Rates of Antibiotic Action Against *Staphylococcus epidermidis* Biofilms," *ASAIO Trans.*, vol. 37, No. 3, Jul.-Sep. 1991, pp. M160-M162.

Stamm, Walter E., "Catheter-Associated Urinary Tract Infections: Epidemiology, Pathogenesis, and Prevention," *American Journal of Medicine*, vol. 91, No. 3B, Sep. 1991, pp. 65S-71S.

Golomb, Gershon, et al., "Prevention of Bacterial Colonization on Polyurethane in vitro by Incorporated Antibacterial Agent," *Journal of Biomedical Materials Research*, vol. 25, No. 8, Aug. 1991, pp. 937-952.

Mulhall, Anne, "Biofilms and Urethral Catheter Infections," *Nursing Standard*, vol. 5, No. 18, Jan. 23-29, 1991, pp. 26-28.

Chang, Chung Che, et al., "Effect of *Staphylococcus epidermidis* on Adherence of *Pseudomonas aeruginosa* and *Proteus mirabilis* to Polymethyl Methacrylate (PMMA) and Gentamicin-Containing PMMA," *Journal of Orthopaedic Research*, vol. 9, No. 2, Mar. 1991, pp. 284-288.

Liedberg, H., et al., "*Pseudomonas aeruginosa*: Adherence to and Growth on Different Urinary Catheter Coatings," *Internattonal Urology and Nephrology*, vol. 22, No. 5, 1990, pp. 487-492.

Anwar, Hosmin, et al., "Testing the Susceptibility of Bacteria in Biofilms to Antibacterial Agents," *Antimicrobial Agents and Chemotherapy*, Vo. 34, No. 3, 1990, pp. 2043-2046.

Dunne, W. Michael Jr., "Effects of Subinhibitory Concentrations of Vancomycin or Cefamandole on Biofilm Production by Coagulase-Negative Staphylococci," *Antimicrobial Agents and Chemotherapy*, vol. 34, No. 3, Mar. 1990, pp. 390-393.

Doughterty, Steven H., et al., "Endogenous Factors Contributing to Prosthetic Device Infections," *Infectious Disease Clinics of North America*, vol. 3, No. 2, Jun. 1989, pp. 199-209.

U.S. Appl. No. 09/734,639, filed Dec. 12, 2000, Pinchuk et al.

Speer, Anthony C., et al., "Biliary Stent Blockage with Bacterial Biofilm," *Annals of Internal Medicine*, vol. 108, No. 4, Apr. 1998, pp. 546-553.

Liedberg, H., et al., "Silver Coating of Urinary Catheters Prevents Adherence and Growth of *Pseudomonas aeruginosa*," *Urological Research*, vol. 17, No. 6, 1989, pp. 357-358.

Ramsay, J.W.A., et al., "Biofilms, Bacteria, and Bladder Catheters: a Clinical Study," *British Journal of Urology*, vol. 64, No. 4, Oct. 1989, pp. 395-398.

Farber, Bruce F., et al., "The Use of Nonsteroidal Antiinflammatory Drugs to Prevent Adherence of *Staphylococcus epidermidis* to Medical Polymers," *Journal of Infectious Diseases*, vol. 166, No. 4, Oct. 1992, pp. 861-865.

Farber, Bruce F., et al., "*Staphylococcus epidermidis* Extracted Slime Inhibits the Antimicrobial Action of Glycpeptide Antibiotics," *Journal of Infectious Diseases*, Vo., 161, No. 1, Jan. 1990, pp. 37-40.

Donnenfeld, E.D., et al., "Biofilm and Bacterial Adherence Inhibition with Sodium Salicylate," *Investigative Ophthamology & Visual Science*, vol. 35, No. 4, 1994, p. 2164.

Farber, B.F., et al., "*Staphylococcus aureus* Extracted Polysaccharide Interferes with the Antimicrobial Action of Glycopeptide Antibiotics," *Clinical Research*, vol. 38, No. 2, 1990, p. 428A.

Farber, B.F., et al., "Extracted *S. epidermidis* Slime Interferes with the Antimicrobial Action of Glycopeptide Antibiotics," *Clinical Research*, vol. 37, No. 2, 1990, p. 428A.

Farber, B.F., et al., "Unique Properties of *S. epidermidis* Extractable Polysaccharide Slime (SEEP)," *Clinical Research*, vol. 36, No. 3, 1988, p. 455A.

Teichberg, Saul, et al., "Salicylic Acid Decreases Extracellular Biofilm Production by *Staphylococcus epidermidis*: Electron Microscope Analysis," *Journal of Infectious Diseases*, vol. 167, No. 6, 1993, pp. 1501-1503.

Farber, Bruce F., et al., "A Novel Antibiofilm Technology for Contact Lens Solutions," *Ophthalmology*, vol. 102, No. 5, May 1995, pp. 831-836.

Roberts, E.L., et al., "The Role of Sodiuym Salicylate in the Prevention of the Adherence of Acanthamoeba Castellanii to Unworn Contact Lenses," *Investigative. Ophthalmology & Visual Science*, vol. 35, No. 4, 1994, p. 2150.

Donnenfeld, Eric D., et al., "Controlled Evaluation of a Bandage Contact Lens and a Topical Nonsteroidal Antiinflammatory Drug in Treating Traumatic Corneal Abrasions," *Ophthalmology*, vol. 102, No. 6, Jun. 1995, pp. 979-984.

Costerton, J. William, et al., "Bacterial Biofilms in Nature and Disease," *Annual Review of Microbiology*, vol. 41, 1987, pp. 435-464.

Parsons, C. Lowell, et al., "Inhibition of Sodium Urate Crystal Adherence to Bladder Surface by Polysaccharide," Journal of Urology, vol. 134, No. 3, Sep. 1985, pp. 614-616.

Kingston, D., et al., "Self-disinfecting Plastics for Intravenous Catheters and Prosthetic Inserts," *Journal of Hygiene*, Cambridge, vol. 96, 1986, pp. 185-198.

Speer, A.G., et al., The Role of Bacterial Biofilm in Clogging of Bilary Stents, Dept. Gastroenterology, Middesex Hospital, London UK, Dept. Biology, University of Calgary, Alberta, Canada.

Sherman, Stuart, et al., "Stent-induced Pancreatic Ductal and Parenchymal Changes: Correlation of Endoscopic Ultrasound with ERCP," *Gastrointestinal Endoscopy*, vol. 44, No. 3, 1996, pp. 276-282.

Anthony G. Gristina et al., "Bacterial Adherence and the Glycocalyx and Their Role in Musculoskeletal Infection," *Orthopedic Clinics of North America*, vol. 15, No. 3, Jul. 1984, pp. 517-535.

F. Ikeda et al., "Formation of Biofilm by Slime Producing *Staphylococcus epidermidis* and Bactericidal Activity of Cefazolin," *Kansenshogaku Zasshi. Journal of the Japanese Association for Infectious Diseases*, vol. 65, No. 7, Jul. 1991, pp. 875-882.

Percuflex® Tail Plus™ Tapered Ureteral Stent. Boston Scientific. Urology. http://www.bostonscientific.com/med_specialty/deviceDetail.jhtml?task=tskBasicDevice.jhtml&s. Feb. 24, 2004 download.

H.N. Bhargava et al., "Triclosan: Applications and Safety," *American Journal of Infection Control*, vol. 24(3), Jun. 1996, pp. 209-218.

Rhonda D. Jones et al., "Triclosan: A Review of Effectiveness and Safety in Health Care Settings," *American Journal of Infection Control*, vol. 28(2), Apr. 2000, pp. 184-196.

J. Regõs et al., "Antimicrobial Spectrum of Triclosan, a Broad-Spectrum Antimicrobial Agent for Topical Application. II. Comparison with Some Other Antimicrobial Agents," *Dermatologica*, vol. 158, 1979, pp. 72-79.

Stephen Rothenburger et al., "In Vitro Antimicrobial Evaluation of Coated VICRYL* Plus Antibacterial Suture (Coated Polyglactin 910 with Triclosan) Using Zone of Inhibition Assays," *Surgical Infections*, vol. 3, supplement, 2002, pp. S-79-S87.

Edward S. Wong et al., Guideline for Prevention of Catheter-associated Urinary Tract Infections. http://www.cdc.gov. n.d. but before the date of this application.

Allan Ronald, "The Etiology of Urinary Tract Infection: Traditional and Emerging Pathogens," *Dis. Mon.*, vol. 49, 2003, pp. 71-82.

Alain Meyrier, Urinary Tract Infections, vol. II, Chapter 7 of *The Schrier Atlas of Diseases of the Kidney*, ed. Robert W. Schrier, 1999.

Donald P. Griffith et al., "Urease: The Primary Cause of Infection-Induced Kidney Stones," *Investigative Urology*, vol. 13(5), Mar. 1976, pp. 346-350.

D.J. Stickler et al., "Control of Encrustation and Blockage of Foley Catheters," *The Lancet*, vol. 361, Apr. 26, 2003, pp. 1435-1437.

Ciba Specialty Chemicals. Ciba® IRGASAN® DP 300, Ciba® IRGACARE® MP Antimicrobials. Toxicological and ecological data; Official registrations. Jan. 2003. 16 pages.

Ciba Specialty Chemicals. Ciba® IRGASAN® DP 300, Ciba®IRGACARE® MP. Antimicrobial active ingredient for personal care products. 2001. 16 pages.

* cited by examiner

IMPLANTABLE OR INSERTABLE MEDICAL DEVICE RESISTANT TO MICROBIAL GROWTH AND BIOFILM FORMATION

STATEMENT OF RELATED APPLICATION

This is a continuation-in-part of U.S. patent application Ser. No. 10/071,840, filed Feb. 8, 2002 now U.S. Pat. No. 6,887,270, and entitled "Implantable Or Insertable Medical Device Resistant To Microbial Growth And Biofilm Formation," which is incorporated by reference herein in its entirety.

FIELD OF THE INVENTION

The present invention relates to implantable or insertable medical devices that provide resistance to microbial growth on and in the environment of the device and resistance to microbial adhesion and biofilm formation on the device. In another aspect, the present invention relates to methods of manufacturing such implantable or insertable medical devices, particularly to methods of manufacturing such devices that comprise at least one matrix polymer region, an antimicrobial agent for providing resistance to microbial growth and/or a microbial adhesion/biofilm synthesis inhibitor for inhibiting the attachment of microbes and the synthesis and accumulation of biofilm on the surface of the medical device.

BACKGROUND OF THE INVENTION

Implantable or insertable medical devices such as stents made of metallic, polymeric or a composite of metallic and polymeric materials frequently occlude due to microbial colonization and adhesion. This problem is particularly prevalent with medical devices that are adapted to remain implanted for a relatively long-term, i.e., from about 30 days to about 12 months or longer. Microbes such as bacteria often colonize on and around the medical device and, upon attaching to surfaces of the device, proliferate and form aggregates within a complex matrix consisting of extracellular polymeric substances, typically polysaccharides. The mass of attached microorganisms and the associated extracellular polymeric substances is commonly referred to as a biofilm or slime. Antimicrobial agents have difficulty penetrating biofilms and killing and/or inhibiting the proliferation of the microorganisms within the biofilm. The colonization of the microbes on and around the device and the synthesis of the biofilm barrier eventually result in encrustation, occlusion and failure of the device.

Previous approaches to minimize this problem have included the use of low surface energy materials such as Teflon® in implantable medical devices and the use of surface coatings on such medical devices. Surface coatings have typically comprised single antimicrobials or 1-2 antibiotics.

For example, U.S. Pat. No. 5,853,745 discloses an implantable medical device having a durable protective coating layer over an antimicrobial coating layer. The coating layers are formed by applying an antimicrobial coating layer to at least a portion of the surface of the medical device, applying a durable coating over the antimicrobial coating layer, and applying a resilient coating layer over the durable coating layer.

U.S. Pat. No. 5,902,283 discloses a non-metallic antimicrobial impregnated implantable medical device where the antimicrobial composition is applied to the device under conditions where the antimicrobial composition permeates the material of the device.

U.S. Pat. No. 5,772,640 discloses polymeric medical devices that have been impregnated and/or coated with chlorhexidine and triclosan by dipping or soaking the medical device in a solution of a hydrophobic or hydrophilic polymer containing chlorhexidine and triclosan.

Published International Application No. WO 99/47595 discloses a plastics material that can be used in certain medical applications comprising an acrylic polymer containing 5-50% of a rubbery copolymer and a biocidal compound. The patent also discloses adding antimicrobial agent to the polymer melt by means of a liquid injection system.

U.S. Pat. No. 5,679,399 discloses membranes that may include one or more permeable or semipermeable layers containing substances such as biocides. The layers allow the transmission of environmental fluids inwardly and the outward dispersion of the biocides. These membranes may also include a sealing or coating to entrap agents such as biocides therein.

Of the previous approaches, coatings have met with the greatest success because of their proximity to the bacterial environment and hence their active approach to preventing bacterial colonization and attachment. However, this approach has proven inadequate because of the potential for bacterial resistance to a single narrow spectrum active agent, because the amount of active agent that can be incorporated into such coatings is typically low, and/or because externally coated tubular devices release active agents to the environment external to the device but not intraluminally.

In an effort to alleviate the foregoing and other disadvantages of the prior art, Applicants have developed an implantable or insertable medical device suitable for long-term implantation and a method for manufacturing such a device, wherein the device provides resistance to microbial growth on and around the device and/or biofilm formation on the device. The device of the present invention, therefore, overcomes the disadvantages associated with the use of coatings as discussed above, and provides a reduced risk of biofilm fouling that eventually results in encrustation, occlusion and failure of the device.

SUMMARY OF THE INVENTION

One aspect of the present invention is directed to an implantable medical device comprising at least one biocompatible matrix polymer region and bioactive agents comprising an antimicrobial agent, a microbial attachment/biofilm synthesis inhibitor, or both. In some preferred embodiments, the medical device comprises multiple distinct matrix polymer regions. One or more barrier layers at least partially covering a matrix polymer region may also be provided in certain preferred embodiments of the present invention. Preferred antimicrobial agents include triclosan, chlorhexidine and salts or combinations thereof. Other antimicrobial agents include, but are not limited to nitrofurazone, benzalkonium chlorides, silver salts and antibiotics such as rifampin, gentamycin and minocyclin. Preferred microbial attachment/biofilm synthesis inhibitors include salicylic acid and salts and derivatives thereof. A radio-opacifying agent may be optionally included in a matrix polymer region, and one or more therapeutic agents may also be present. The matrix polymer and any barrier layer may preferably comprise a biodegradable or substantially non-biodegradable material such as an ethylene vinyl acetate copolymer, copolymers of ethylene with acrylic acid or methacrylic acid; metallocene catalyzed polyethylenes and polyethylene copolymers, ionomers, elastomeric materials such as elastomeric polyurethanes and polyurethane copolymers, silicones and mixtures thereof.

Among medical devices in accordance with the present invention are biliary, ureteral, urethral and pancreatic stents, stent covers, catheters, venous access devices and devices bridging or providing drainage between a sterile and non-sterile body environment or between two sterile body environments. Pancreatic stents that release a buffering agent are among preferred pancreatic stents.

In another aspect, the present invention is directed to a method of manufacturing an implantable or insertable medical device comprising providing one or more biocompatible matrix polymers and one or more bioactive agents comprising an antimicrobial agent and/or a microbial attachment/biofilm synthesis inhibitor; processing the one or more biocompatible matrix polymers and the one or more bioactive agents under conditions that substantially prevent preferential partitioning of any of the bioactive agents to a surface of any of the biocompatible matrix polymers and substantially prevent chemical modification of the one or more bioactive agents. Processing preferably comprises forming a homogenous mixture of the matrix polymer and any bioactive agent and optional radio-opacifying agent and/or therapeutic agent and shaping the homogeneous mixture into at least a portion of an implantable or insertable medical device. Among preferred shaping processes are included extrusion and coextrusion for multiple layer structures or for partitioning of the medical device into different polymer matrix sections (e.g., sections of different durometer values).

BRIEF DESCRIPTION OF THE DRAWINGS

As is typically the case with such figures, FIGS. 1, 2 and 12 are simplified schematic representations presented for purposes of illustration only, and the actual structures may differ in numerous respects including the relative scale of the components.

DETAILED DESCRIPTION OF THE INVENTION

Figure 1:
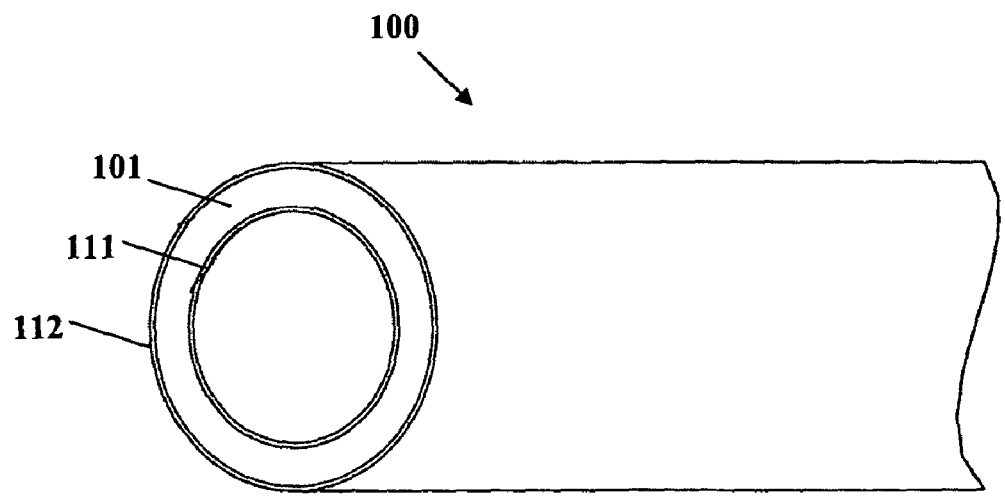
FIG. 1 is a simplified schematic representation (perspective view) of a portion of an implantable or insertable medical device in accordance with an embodiment of the present invention.

In one aspect, the present invention is directed to an implantable or insertable medical device comprising at least one biocompatible matrix polymer region, as well as one or multiple bioactive components, which comprise an antimicrobial agent and/or a microbial attachment/biofilm synthesis inhibitor.

The term "biocompatible" as used herein describes a material that is substantially not toxic to the human body, and that does not significantly induce inflammation or other adverse response in body tissues.

The term "matrix polymer" as used herein refers to a polymeric material that forms at least a portion or region of the implantable or insertable medical device of the present invention. The matrix polymer is selected to be biocompatible and provide mechanical properties consistent with the intended function and operation of the implantable or insertable medical device. The matrix polymer also serves as a repository in which at least one and, in some preferred embodiments, both the antimicrobial agent and microbial attachment/biofilm synthesis inhibitor are dispersed and/or dissolved. The matrix polymer may also contain, as further optional components, a radio-opacifying agent and/or one or more therapeutic agents.

The term "antimicrobial agent" as used herein means a substance that kills and/or inhibits the proliferation and/or growth of microbes, particularly bacteria, fungi and yeast. Antimicrobial agents, therefore, include biocidal agents and biostatic agents as well as agents that possess both biocidal and biostatic properties. In the context of the present invention, the antimicrobial agent kills and/or inhibits the proliferation and/or growth of microbes on and around the surfaces of an implanted medical device.

The term "microbial attachment/biofilm synthesis inhibitor" as used herein means a substance that inhibits the attachment of microbes onto a surface and the ability of such microbes to synthesize and/or accumulate biofilm on a surface. In the context of the present invention, such a surface includes a surface of an implantable medical device exposed to a physiological environment, such as a physiological fluid, that may be conducive to the formation and accumulation of biofilm on the surface of the medical device. The microbial attachment/biofilm synthesis inhibitor may also have substantial antimicrobial activity as described herein. Likewise, the antimicrobial agent may also have substantial ability to inhibit microbial attachment/biofilm synthesis.

By "biofilm" is meant the mass of microorganisms attached to a surface, such as a surface of a medical device, and the associated extracellular substances produced by one or more of the attached microorganisms. The extracellular substances are typically polymeric substances and commonly comprise a matrix of complex polysaccharides, proteinaceous substances and glycopeptides. This matrix or biofilm is also commonly referred to as "glycocalyx."

Biofilm formation on the surfaces of implantable or insertable medical devices adapted for long-term implantation, e.g., from about 30 days to 12 months or longer, can result in eventual encrustation and failure of the device. Further, the proliferation of microbes within the biofilm can lead to localized infections as well as difficult to treat systemic infections. The extracellular substances that comprise the biofilm matrix can act as a barrier that protects and isolates the microorganisms housed in the biofilm from normal immunological defense mechanisms, such as antibodies and phagocytes, as well as from antimicrobial agents including surfactants, biocides and antibiotics. The biofilm also facilitates the growth and proliferation of microbes housed within the biofilm.

The present invention substantially reduces the risk of biofilm accumulation on the surfaces of a medical device adapted for long term implantation, and the resultant likelihood of premature failure of the device due to encrustation and occlusion by such biofilm. In some preferred embodiments of the present invention, the medical device is intended to remain implanted for a relatively long period of from about 30 days to about 12 months or longer. However, it is understood that the device may be implanted for a period of 30 days or shorter as well.

The biocompatible matrix polymer of the device of the present invention is provided to serve as a repository in which the antimicrobial agent, the microbial attachment/biofilm synthesis inhibitor, or both, are dispersed and/or dissolved. The medical device of the present invention will preferably contain at least one matrix polymer which forms at least a single distinct portion or region of the medical device. Where only a single distinct matrix polymer region is provided in the medical device, the matrix polymer will preferably contain one or both of the antimicrobial agent and the microbial attachment/biofilm synthesis inhibitor. However, in other preferred embodiments, the medical device will comprise two or more distinct matrix polymer regions. The distinct regions may exist, e.g., as coaxial layers or as distinct sections lengthwise along the longitudinal axis of the device (e.g., a stent having distinct end regions of different durometer value with a transitional coextruded region in between). Where two or more distinct matrix polymer regions are present in a medical device that contains both the antimicrobial agent and the microbial attachment/biofilm synthesis inhibitor, it is not necessary that both bioactive agents be present in any single one of such multiple matrix polymer regions. Thus, the antimicrobial agent may be present in a first matrix polymer region and the microbial attachment/biofilm synthesis inhibitor may be present in a second matrix polymer region distinct from the first matrix polymer region. However, it is understood that one or both bioactive agents may be present in one or all of any distinct matrix polymer regions. Further, as discussed more fully below, where multiple distinct matrix polymer regions are present, the regions may be separated by barrier layers that at least partially cover a surface of the matrix polymer region.

The amount of the antimicrobial agent present in a matrix polymer is preferably an amount effective to kill and/or inhibit the growth of microbes on and around the implanted medical device. Preferred amounts of the antimicrobial agent present in the matrix polymer range from about 0.1% to about 25% by weight of the matrix polymer. Amounts of from about 10% to about 25% by weight of the matrix polymer are particularly preferred.

The amount of the microbial attachment/biofilm synthesis inhibitor present in a matrix polymer is preferably an amount effective to inhibit the attachment of microbes onto and the synthesis and/or accumulation of biofilm by attached microbes on a surface of the implanted medical device. Preferred amounts of the microbial attachment/biofilm synthesis inhibitor present in the matrix polymer range from about 0.1% to about 25% by weight of the matrix polymer. Amounts of from about 10% to about 25% by weight of the matrix polymer are particularly preferred.

The amount of antimicrobial agent and/or microbial attachment/biofilm synthesis inhibitor present in a matrix polymer will depend on, inter alia, on the efficacy of the bioactive agent employed, the length of time during which the medical device is intended to remain implanted, as well as the rate at which the matrix polymer or barrier layer releases the bioactive agent into the environment of the implanted medical device. Thus, a device that is intended to remain implanted for a longer period will generally require a higher percentage of the antimicrobial agent and/or microbial attachment/biofilm synthesis inhibitor. Similarly, a matrix polymer that provides faster release of the bioactive agent may require a higher amount of the bioactive agent. The amount of bioactive agent in the matrix polymer may be limited, of course, by the propensity for such bioactive agent to cause undesirable localized or systemic toxic reaction and by the potential impairment of the mechanical properties necessary for the proper functioning of the medical device.

In many instances, it is believed that the bioactive agent is released, at least in part, from a non-biodegradable matrix polymer region by a mechanism wherein the matrix polymer imbibes or contacts physiological fluid. The physiological fluid dissolves or disperses the bioactive agent reposed within the matrix, and the dissolved or dispersed bioactive agent then diffuses outwardly from the matrix polymer into the physiological environment where the device is implanted. Matrix polymers need not be permeable to aqueous fluids such as physiological fluids to provide release of bioactive agent. Matrix polymers with low permeability to aqueous fluids may adsorb such fluids at a surface of the polymer. In such matrix polymers, a concentration gradient is believed to be set up at the surface of the polymer and the bioactive agent is released via diffusion based on its affinity for the solid polymer relative to its solubility in the fluid or aqueous phase. Where the matrix polymer is biodegradable, similar diffusion processes may also occur. In a biodegradable matrix polymer, bioactive agent may also be released as the biodegradable matrix polymer containing the reposed bioactive agent biodegrades upon contact with the physiological environment where the device is implanted. Thus, in a biodegradable polymer, bioactive agent may be released by diffusional processes and upon biodegradation of the polymer matrix.

The antimicrobial agent present in the matrix polymer can be any pharmaceutically acceptable antimicrobial agent. By "pharmaceutically acceptable" as used herein is meant an agent that is approved or capable of being approved by the United States Food and Drug Administration or Department of Agriculture as safe and effective for use in humans or animals when incorporated in or on an implantable or insertable medical device. Preferred antimicrobial agents include, but are not limited to, triclosan, chlorhexidine, nitrofurazone, benzalkonium chlorides, silver salts and antibiotics such as rifampin, gentamycin and minocyclin and combinations thereof.

The microbial attachment/biofilm synthesis inhibitor can be any pharmaceutically acceptable agent that inhibits the attachment of microbes onto and the synthesis and/or accumulation of biofilm on a surface of an implantable or insertable medical device. Among preferred microbial attachment/biofilm synthesis inhibitors include, but are not limited to, non-steroidal anti-inflammatory drugs (NSAIDs) and chelating agents such as EDTA (ethylenediaminetetraacetic acid), EGTA (O,O'-bis(2-aminoethyl)ethyleneglycol-N,N,N',N'-tetraacetic acid) and mixtures thereof. Among preferred NSAIDs are salicylic acid and salts and derivatives thereof. Preferred salts of salicylic acid include, but are not limited to, sodium salicylate and potassium salicylate. Sodium salicylate is a particularly preferred salt for use as the microbial attachment/biofilm synthesis inhibitor. Salicylic acid is a particularly preferred microbial attachment/biofilm synthesis inhibitor.

Some preferred combinations of antimicrobial agent and microbial attachment/biofilm synthesis inhibitors present in a medical device in accordance with the present invention comprise triclosan and/or chlorhexidine in combination with salicylic acid or a salt thereof such as sodium salicylate. A particularly preferred combination comprises triclosan and salicylic acid or a salt thereof.

The presence of both an antimicrobial agent and/or a microbial attachment/biofilm synthesis inhibitor in a medical device in accordance with the present invention can provide distinct advantages in some embodiments over the use of, for example, only an antimicrobial agent. The use of such a dual mechanism for preventing microbial attachment and colonization is believed to have a synergistic effect. The synergy is related to the different mechanism of action of each of the bioactive agents. The antimicrobial agent not only kills a large percentage of microbes approaching a surface of the device, it also reduces the burden of microbes upon which the microbial attachment/biofilm synthesis inhibitor must act. Moreover, microbes that have attached to a surface produce a protective biofilm barrier after attachment. This biofilm barrier prevents or reduces the ability of antimicrobial agents from reaching the microbes. The antimicrobial agent is thereby rendered substantially less effective upon formation of the biofilm barrier. Therefore, if microbial attachment is prevented, biofilm synthesis is inhibited and the antimicrobial agent is rendered more effective.

The matrix polymer used in the implantable or insertable medical device of the present invention may be any biocompatible polymer suitable for use in implantable or insertable medical devices. The matrix polymer may be substantially non-biodegradable or biodegradable.

Preferred substantially non-biodegradable biocompatible matrix polymers include thermoplastic and elastomeric polymeric materials. Polyolefins such as metallocene catalyzed polyethylenes, polypropylenes, and polybutylenes and copolymers thereof; vinyl aromatic polymers such as polystyrene; vinyl aromatic copolymers such as styrene-isobutylene copolymers and butadiene-styrene copolymers; ethylenic copolymers such as ethylene vinyl acetate (EVA), ethylene-methacrylic acid and ethylene-acrylic acid copolymers where some of the acid groups have been neutralized with either zinc or sodium ions (commonly known as ionomers); polyacetals; chloropolymers such as polyvinylchloride (PVC); fluoropolymers such as polytetrafluoroethylene (PTFE); polyesters such as polyethyleneterephthalate (PET); polyester-ethers; polyamides such as nylon 6 and nylon 6,6; polyamide ethers; polyethers; elastomers such as elastomeric polyurethanes and polyurethane copolymers; silicones; polycarbonates; and mixtures and block or random copolymers of any of the foregoing are non-limiting examples of non-biodegradable biocompatible matrix polymers useful for manufacturing the medical devices of the present invention.

Among particularly preferred non-biodegradable polymeric materials are polyolefins, ethylenic copolymers including ethylene vinyl acetate copolymers (EVA) and copolymers of ethylene with acrylic acid or methacrylic acid; elastomeric polyurethanes and polyurethane copolymers; metallocene catalyzed polyethylene (mPE), mPE copolymers, ionomers, and mixtures and copolymers thereof; and vinyl aromatic polymers and copolymers. Among preferred vinyl aromatic copolymers are included copolymers of polyisobutylene with polystyrene or polymethylstyrene, even more preferably polystyrene-polyisobutylene-polystyrene triblock copolymers. These polymers are described, for example, in U.S. Pat. No. 5,741,331, U.S. Pat. No. 4,946,899 and U.S. Ser. No. 09/734,639, each of which is hereby incorporated by reference in its entirety. Ethylene vinyl acetate having a vinyl acetate content of from about 19% to about 28% is an especially preferred non-biodegradable material. EVA copolymers having a lower vinyl acetate content of from about 3% to about 15% are also useful in particular embodiments of the present invention as are EVA copolymers having a vinyl acetate content as high as about 40%. These relatively higher vinyl acetate content copolymers may be beneficial in offsetting stiffness from coextruded barrier layers. Among preferred elastomeric polyurethanes are block and random copolymers that are polyether based, polyester based, polycarbonate based, aliphatic based, aromatic based and mixtures thereof. Commercially available polyurethane copolymers include, but are not limited to, Carbothane®, Tecoflex®, Tecothane®, Tecophilic®, Tecoplast®, Pellethane®, Chronothane® and Chronoflex®. Other preferred elastomers include polyester-ethers, polyamide-ethers and silicone.

Among preferred biodegradable matrix polymers are included, but not limited to, polylactic acid, polyglycolic acid and copolymers and mixtures thereof such as poly(L-lactide) (PLLA), poly(D,L-lactide) (PLA); polyglycolic acid [polyglycolide (PGA)], poly(L-lactide-co-D,L-lactide) (PLLA/PLA), poly(L-lactide-co-glycolide) (PLLA/PGA), poly(D,L-lactide-co-glycolide) (PLA/PGA), poly(glycolide-co-trimethylene carbonate) (PGA/PTMC), poly(D,L-lactide-co-caprolactone) (PLA/PCL), poly(glycolide-co-caprolactone) (PGA/PCL); polyethylene oxide (PEO), polydioxanone (PDS), polypropylene fumarate, poly(ethyl glutamate-co-glutamic acid), poly(tert-butyloxy-carbonylmethyl glutamate), polycaprolactone (PCL), polycaprolactone co-butylacrylate, polyhydroxybutyrate (PHBT) and copolymers of polyhydroxybutyrate, poly(phosphazene), poly(phosphate ester), poly(amino acid) and poly(hydroxy butyrate), polydepsipeptides, maleic anhydride copolymers, polyphosphazenes, polyiminocarbonates, poly[(97.5% dimethyl-trimethylene carbonate)-co-(2.5% trimethylene carbonate)], cyanoacrylate, polyethylene oxide, polyvinyl alcohol (PVA), polyvinylpyrrolidone (PVP), chemically modified celluloses such as hydroxypropylmethylcellulose and regenerate cellulose, polysaccharides such as hyaluronic acid, chitosan, alginates and modified starch such as pentastarch and hydroxyethyl starch, proteins such as gelatin and collagen, and mixtures and copolymers thereof, among others.

Particularly preferred biodegradable polymers comprise polylactic acid, polyglycolic acid and copolymers and mixtures thereof.

The medical device of the present invention may also contain a radio-opacifying agent within its structure. For example, the radio-opacifying agent may be present in or on any of the matrix polymer regions or in or on an optional barrier layer that at least partially covers a surface of a matrix polymer region. Barrier layers are described more fully below. The radio-opacifying agent facilitates viewing of the medical device during insertion of the device and at any point while the device is implanted. A radio-opacifying agent typically functions by scattering x-rays. The areas of the medical device that scatter the x-rays are detectable on a radiograph. Among radio-opacifying agents useful in the medical device of the present invention are included, but not limited to, bismuth subcarbonate, bismuth oxychloride, bismuth trioxide, barium sulfate, tungsten and mixtures thereof. Where present, the radio-opacifying agent is preferably present in an amount of from about 0.5% to about 90%, more preferably from about 10% to about 90% by weight, of the matrix polymer. A particularly preferred amount of radio-opacifying agent is from about 10 to about 40% by weight of the matrix polymer.

The medical device of the present invention may also contain one or more therapeutic agents within its structure. For example, any therapeutic agent may be present in or on any of the matrix polymer regions or in or on any optional barrier layer that at least partially covers a surface of a matrix polymer region. The therapeutic agent may be any pharmaceutically acceptable synthetic or non-synthetic agent. A therapeutic agent includes genetic therapeutic agents, non-genetic therapeutic agents and cells.

Exemplary non-genetic therapeutic agents include: (a) anti-thrombotic agents such as heparin, heparin derivatives, urokinase, and PPack (dextrophenylalanine proline arginine chloromethylketone); (b) steroidal and non-steroidal anti-inflammatory agents (NSAIDs) such as dexamethasone, prednisolone, corticosterone, hydrocortisone and budesonide estrogen, sulfasalazine and mesalamine, salicylic acid and salts and derivatives thereof, ibuprofen, naproxen, sulindac, diclofenac, piroxicam, ketoprofen, diflunisal, nabumetone, etodolac, oxaprozin and indomethacin; (c) chemotherapeutic agents such as antineoplastic/antiproliferative/anti-mitotic agents including paclitaxel, 5-fluorouracil, cisplatin, vinblastine, vincristine, epothilones, endostatin, angiostatin, doxorubicin, methotrexate, angiopeptin, monoclonal antibodies capable of blocking smooth muscle cell proliferation, and thymidine kinase inhibitors; (d) anesthetic agents such as lidocaine, bupivacaine and ropivacaine; (e) anti-coagulants such as D-Phe-Pro-Arg chloromethyl ketone, an RGD peptide-containing compound, heparin, hirudin, antithrombin compounds, platelet receptor antagonists, anti-thrombin antibodies, anti-platelet receptor antibodies, aspirin, prostaglandin inhibitors, platelet inhibitors and tick antiplatelet peptides; (f) vascular cell growth promoters such as growth factors, transcriptional activators, and translational promotors; (g) vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; (h) protein kinase and tyrosine kinase inhibitors (e.g., tyrphostins, genistein, quinoxalines); (i) prostacyclin analogs; (j) cholesterol-lowering agents; (k) angiopoietins; (l) antimicrobial agents such as triclosan, cephalosporins, β-lactams, aminoglycosides and nitrofurantoin; (m) chemotherapeutic agents such as cytotoxic agents, cytostatic agents and cell proliferation affectors; (n) vasodilating agents; (o) agents that interfere with endogenous vasoactive mechanisms; (p) inhibitors of leukocyte recruitment, such as monoclonal antibodies; (q) cytokines; (r) hormones; (s) analgesics; (t) local anesthetic agents; and (u) antispasmodic agents.

Examples of non-steroidal anti-inflammatory drugs, not necessarily exclusive of those listed above, include aminoarylcarboxylic acid derivatives such as enfenamic acid, etofenamate, flufenamic acid, isonixin, meclofenamic acid, mefanamic acid, niflumic acid, talniflumate, terofenamate and tolfenamic acid; arylacetic acid derivatives such as acemetacin, alclofenac, amfenac, bufexamac, cinmetacin, clopirac, diclofenac sodium, etodolac, felbinac, fenclofenac, fenclorac, fenclozic acid, fentiazac, glucametacin, ibufenac, indomethacin, isofezolac, isoxepac, lonazolac, metiazinic acid, oxametacine, proglumetacin, sulindac, tiaramide, tolmetin and zomepirac; arylbutyric acid derivatives such as bumadizon, butibufen, fenbufen and xenbucin; arylcarboxylic acids such as clidanac, ketorolac (the tromethamine salt thereof is sold under the commercial name Toradol®) and tinoridine; arylpropionic acid derivatives such as alminoprofen, benoxaprofen, bucloxic acid, carprofen, fenoprofen, flunoxaprofen, flurbiprofen, ibuprofen, ibuproxam, indoprofen, ketoprofen, loxoprofen, miroprofen, naproxen, oxaprozin, piketoprofen, pirprofen, pranoprofen, protizinic acid, suprofen and tiaprofenic acid; pyrazoles such as difenamizole and epirizole; pyrazolones such as apazone, benzpiperylon, feprazone, mofebutazone, morazone, oxyphenbutazone, phenybutazone, pipebuzone, propyphenazone, ramifenazone, suxibuzone and thiazolinobutazone; salicylic acid and its derivatives such as acetaminosalol, aspirin, benorylate, bromosaligenin, calcium acetylsalicylate, diflunisal, etersalate, fendosal, gentisic acid, glycol salicylate, imidazole salicylate, lysine acetylsalicylate, mesalamine, morpholine salicylate, 1-naphthyl salicylate, olsalazine, parsalmide, phenyl acetylsalicylate, phenyl salicylate, salacetamide, salicylamine o-acetic acid, salicylsulfuric acid, salsalate and sulfasalazine; thiazinecarboxamides such as droxicam, isoxicam, piroxicam and tenoxicam; others such as ε-acetamidocaproic acid, s-adenosylmethionine, 3-amino-4-hydroxybutyric acid, amixetrine, bendazac, benzydamine, bucolome, difenpiramide, ditazol, emorfazone, guaiazulene, nabumetone, nimesulide, orgotein, oxaceprol, paranyline, perisoxal, pifoxime, proquazone, proxazole and tenidap; and pharmaceutically acceptable salts thereof.

Examples of steroidal anti-inflammatory agents (glucocorticoids), not necessarily exclusive of those listed above, include 21-acetoxyprefnenolone, aalclometasone, algestone, amicinonide, beclomethasone, betamethasone, budesonide, chloroprednisone, clobetasol, clobetasone, clocortolone, cloprednol, corticosterone, cortisone, cortivazol, deflazacort, desonide, desoximetasone, dexamethasone, diflorasone, diflucortolone, difluprednate, enoxolone, fluazacort, flucloronide, flumehtasone, flunisolide, fluocinolone acetonide, fluocinonide, fluocortin butyl, fluocortolone, fluorometholone, fluperolone acetate, fluprednidene acetate, fluprednisolone, flurandrenolide, fluticasone propionate, formocortal, halcinonide, halobetasol priopionate, halometasone, halopredone acetate, hydrocortamate, hydrocortisone, loteprednol etabonate, mazipredone, medrysone, meprednisone, methyolprednisolone, mometasone furoate, paramethasone, prednicarbate, prednisolone, prednisolone 25-diethylaminoacetate, prednisone sodium phosphate, prednisone, prednival, prednylidene, rimexolone, tixocortal, triamcinolone, triamcinolone acetonide, triamcinolone benetonide, triamcinolone hexacetonide, and pharmaceutically acceptable salts thereof.

Analgesic agents include narcotic and non-narcotic analgesics. Narcotic analgesic agents include alfentanil, allylprodine, alphaprodine, anileridine, benzylmorphine, bezitramide, buprenorphine, butorphanol, clonitazene, codeine, codeine methyl bromide, codeine phosphate, codeine sulfate, desomorphine, dextromoramide, dezocine, diampromide, dihydrocodeine, dihydrocodeinone enol acetate, dihydromorphine, dimenoxadol, dimepheptanol, dimethylthiambutene, dioxaphetyl butyrate, dipipanone, eptazocine, ethoheptazine, ethylmethlythiambutene, ethylmorphine, etonitazene, fentanyl, hydrocodone, hydromorphone, hydroxypethidine, isomethadone, ketobemidone, levorphanol, lofentanil, meperidine, meptazinol, metazocine, methadone hydrochloride, metopon, morphine, myrophine, nalbuphine, narceine, nicomorphine, norlevorphanol, normethadone, normorphine, norpipanone, opium, oxycodone, oxymorphone, papaveretum, pentazocine, phenadoxone, phenazocine, pheoperidine, piminodine, piritramide, proheptazine, promedol, properidine, propiram, propoxyphene, rumifentanil, sufentanil, tilidine, and pharmaceutically acceptable salts thereof. Non-narcotic analgesics include aceclofenac, acetaminophen, acetaminosalol, acetanilide, acecylsalicylsalicylic acid, alclofenac, alminoprofen, aloxiprin, aluminum bis(acetylsalicylate), aminochlorthenoxazin, 2-amino-4 picoline, aminopropylon, aminopyrine, ammonium salicylate, amtolmetin guacil, antipyrine, antipyrine salicylate, antrafenine, apazone, aspirin, benorylate, benoxaprofen, benzpiperylon, benzydamine, bermoprofen, brofenac, p-bromoacetanilide, 5-bromosalicylic acid acetate, bucetin, bufexamac, bumadizon, butacetin, calcium acetylsalicylate, carbamazepine, carbiphene, carsalam, chloralantipyrine, chlorthenoxazin(e), choline salicylate, cinchophen, ciramadol, clometacin, cropropamide, crotethamide, dexoxadrol, difenamizole, diflunisal, dihydroxyaluminum acetylsalicylate, dipyrocetyl, dipyrone, emorfazone, enfenamic acid, epirizole, etersalate, ethenzamide, ethoxazene, etodolac, felbinac, fenoprofen, floctafenine, flufenamic acid, fluoresone, flupirtine, fluproquazone, flurbiprofen, fosfosal, gentisic acid, glafenine, ibufenac, imidazole salicylate, indomethacin, indoprofen, isofezolac, isoladol, isonixin, ketoprofen, ketorolac, p-lactophenetide, lefetamine, loxoprofen, lysine acetylsalicylate, magnesium acetylsalicylate, methotrimeprazine, metofoline, miroprofen, morazone, morpholine salicylate, naproxen, nefopam, nifenazone, 5' nitro-2' propoxyacetanilide, parsalmide, perisoxal, phenacetin, phenazopyridine hydrochloride, phenocoll, phenopyrazone, phenyl acetylsalicylate, phenyl salicylate, phenyramidol, pipebuzone, piperylone, prodilidine, propacetamol, propyphenazone, proxazole, quinine salicylate, ramifenazone, rimazolium metilsulfate, salacetamide, salicin, salicylamide, salicylamide o-acetic acid, salicylsulfuric acid, salsalte, salverine, simetride, sodium salicylate, sulfamipyrine, suprofen, talniflumate, tenoxicam, terofenamate, tetradrine, tinoridine, tolfenamic acid, tolpronine, tramadol, viminol, xenbucin, zomepirac, and pharmaceutically acceptable salts thereof.

Local anesthetic agents include amucaine, amolanone, amylocaine hydrochloride, benoxinate, benzocaine, betoxycaine, biphenamine, bupivacaine, butacaine, butaben, butanilicaine, butethamine, butoxycaine, carticaine, chloroprocaine hydrochloride, cocaethylene, cocaine, cyclomethycaine, dibucaine hydrochloride, dimethisoquin, dimethocaine, diperadon hydrochloride, dyclonine, ecgonidine, ecgonine, ethyl chloride, beta-eucaine, euprocin, fenalcomine, fomocaine, hexylcaine hydrochloride, hydroxytetracaine, isobutyl p-aminobenzoate, leucinocaine mesylate, levoxadrol, lidocaine, mepivacaine, meprylcaine, metabutoxycaine, methyl chloride, myrtecaine, naepaine, octacaine, orthocaine, oxethazaine, parethoxycaine, phenacaine hydrochloride, phenol, piperocaine, piridocaine, polidocanol, pramoxine, prilocaine, procaine, propanocaine, proparacaine, propipocaine, propoxycaine hydrochloride, pseudococaine, pyrrocaine, ropavacaine, salicyl alcohol, tetracaine hydrochloride, tolycaine, trimecaine, zolamine, and pharmaceutically acceptable salts thereof.

Antispasmodic agents include alibendol, ambucetamide, aminopromazine, apoatropine, bevonium methyl sulfate, bietamiverine, butaverine, butropium bromide, n-butylscopolammonium bromide, caroverine, cimetropium bromide, cinnamedrine, cleboride, coniine hydrobromide, coniine hydrochloride, cyclonium iodide, difemerine, diisopromine, dioxaphetyl butyrate, diponium bromide, drofenine, emepronium bromide, ethaverine, feclemine, fenalamide, fenoverine, fenpiprane, fenpiverinium bromide, fentonium bromide, flavoxate, flopropione, gluconic acid, guaiactamine, hydramitrazine, hymecromone, leiopyrrole, mebeverine, moxaverine, nafiverine, octamylamine, octaverine, 4-diethylamino-2-butynylphenylcyclohexylglycolate (e.g., 4-diethylamino-2-butynylphenylcyclohexylglycolate hydrochloride, also known as oxybutynin chloride, sold under the commercial name Ditropan®), pentapiperide, phenamacide hydrochloride, phloroglucinol, pinaverium bromide, piperilate, pipoxolan hydrochloride, pramiverin, prifinium bromide, properidine, propivane, propyromazine, prozapine, racefemine, rociverine, spasmolytol, stilonium iodide, sultroponium, tiemonium iodide, tiquizium bromide, tiropramide, trepibutone, tricromyl, trifolium, trimebutine, n,n-1trimethyl-3,3-diphenyl-propylamine, tropenzile, trospium chloride, xenytropium bromide, and pharmaceutically acceptable salts thereof.

Exemplary genetic therapeutic agents include anti-sense DNA and RNA as well as DNA coding for: (a) anti-sense RNA, (b) tRNA or rRNA to replace defective or deficient endogenous molecules, (c) angiogenic and other factors including growth factors such as acidic and basic fibroblast growth factors, vascular endothelial growth factor, endothelial mitogenic growth factors, epidermal growth factor, transforming growth factor α and β, platelet-derived endothelial growth factor, platelet-derived growth factor, tumor necrosis factor α, hepatocyte growth factor and insulin-like growth factor, (d) cell cycle inhibitors including CD inhibitors, and (e) thymidine kinase ("TK") and other agents useful for interfering with cell proliferation. Also of interest is DNA encoding for the family of bone morphogenic proteins ("BMP's"), including BMP-2, BMP-3, BMP-4, BMP-5, BMP-6 (Vgr-1), BMP-7 (OP-1), BMP-8, BMP-9, BMP-10, BMP-11, BMP-12, BMP-13, BMP-14, BMP-15, and BMP-16. Currently preferred BMP's are any of BMP-2, BMP-3, BMP-4, BMP-5, BMP-6 and BMP-7. These dimeric proteins can be provided as homodimers, heterodimers, or combinations thereof, alone or together with other molecules. Alternatively, or in addition, molecules capable of inducing an upstream or downstream effect of a BMP can be provided. Such molecules include any of the "hedgehog" proteins, or the DNA's encoding them.

Vectors of interest for delivery of genetic therapeutic agents include viral vectors such as adenoviruses, gutted adenoviruses, adeno-associated virus, retroviruses, alpha virus (Semliki Forest, Sindbis, etc.), lentiviruses, herpes simplex virus, replication competent viruses (e.g., ONYX-015) and hybrid vectors; and non-viral vectors such as artificial chromosomes and mini-chromosomes, plasmid DNA vectors (e.g., pCOR), cationic polymers (e.g., polyethyleneimine, polyethyleneimine (PEI)), graft copolymers (e.g., polyether-PEI and polyethylene oxide-PEI), neutral polymers such as polyvinylpyrrolidone (PVP) and SP1017 (SUPRATEK), lipids such as cationic lipids, liposomes, lipoplexes, nanoparticles, or microparticles, with and without targeting sequences such as the protein transduction domain (PTD).

Cells include cells of human origin (autologous or allogeneic), including whole bone marrow, bone marrow derived mono-nuclear cells, progenitor cells (e.g., endothelial progenitor cells), stem cells (e.g., mesenchymal, hematopoietic, neuronal), pluripotent stem cells, fibroblasts, myoblasts, satellite cells, pericytes, cardiomyocytes, skeletal myocytes or macrophage, or from an animal, bacterial or fungal source (xenogeneic), which can be genetically engineered if desired to deliver proteins of interest.

Among preferred therapeutic agents that may optionally be present in a medical device of the present invention include, but are not limited to, steroidal and non-steroidal anti-inflammatory agents (NSAIDs) and chemotherapeutic agents such as antineoplastic/antiproliferative/anti-mitotic agents, cytotoxic agents, cytostatic agents and cell proliferation affectors.

Examples of chemotherapeutic agents include cisplatin, methotrexate, doxorubicin, paclitaxel and docetaxel. Examples of steroidal anti-inflammatory agents include dexamethasone, hydrocortisone and prednisone.

The therapeutic agent may be applied onto or into the device or any portion thereof (the matrix polymer region or any optional barrier layer, for example) by contacting the device or portion thereof with a solution or suspension of the therapeutic agent, for example by spraying, dipping, and so forth, followed by evaporating the solvent or carrier liquid. The drug may also be incorporated during the processing and/or shaping of any of the matrix polymers and/or optional polymeric barrier layers used to form the medical device of the present invention provided that the drug is stable at the conditions (e.g., temperature and pressure) required during such processing and/or shaping.

The amount of the therapeutic agent will be a therapeutically effective amount. As with the antimicrobial agent and microbial attachment/biofilm synthesis inhibitor, the amount of any therapeutic agent present in a medical device will depend, inter alia, on the particular therapeutic agent, the length of time during which the medical device is intended to remain implanted, and the rate at which the therapeutic agent is released from the matrix polymer and/or barrier layer. The amount of the therapeutic agent may be limited by the propensity of such agent to cause an undesirable localized or systemic toxic reaction and by the impairment of mechanical properties necessary for proper functioning of the device.

The medical device of the present invention may comprise a multilayer structure comprising from 2 to about 50 distinct layers, more preferably from about 2 to about 20 layers formed by coextrusion as described more fully below. Preferred multilayer structures may have from about 2 to about 7 distinct layers. Particularly preferred multilayer structures have from about 3 to about 7 layers, with a 3 layer construction being especially preferred. As noted above, the medical device comprises one or more matrix polymer regions. The medical device can also comprise one or more barrier regions as well. Hence, in a multilayer construction, one or more of the distinct layers may be a barrier layer that least partially covers one or more matrix polymer layers. Thus, the medical device of the present invention may comprise one or more layers comprising one or more distinct matrix polymer layers and, if desired, one or more barrier layers.

Multilayer structures of the present invention need not comprise a barrier layer. For example, a medical device in accordance with the present invention may comprise a two-layer structure comprising a first matrix polymer layer containing the one or more bioactive agents and a further optional radio-opacifying agent and a second layer on an external surface of the first matrix polymer layer wherein the second layer provides lubricity. Such a lubricious layer may be desirable, for example, to facilitate insertion and implantation of the medical device (e.g., a hydrophilic coating layer such as Hydroplus™ coating (Union Carbide)).

It is understood that the medical device of the present invention is not limited to a multiple layer structure and, indeed, a single layer structure such as an annular tube comprising a matrix polymer or lengthwise sections of differing matrix polymers, an antimicrobial agent and/or a microbial attachment/biofilm synthesis inhibitor and an optional radio-opacifying agent, is within the scope of the present invention.

Medical devices in accordance with the present invention having multiple layer structures may provide certain advantages relative to single layer devices, however. For example, a barrier layer can be provided to control the rate of release of bioactive material or therapeutic agent from an adjacent layer, such a matrix polymer layer. The barrier layer, as described more fully below, may also be advantageous in substantially reducing the partitioning of a bioactive agent to the surface of a matrix polymer layer during processing. Multiple layers, such as distinct matrix polymer layers, may also act as reservoirs for different bioactive agents and/or combinations of a bioactive agent, a radio-opaque material and a therapeutic agent. Hence, the use of multiple layers may be advantageous in providing different release profiles of different bioactive agents and/or therapeutic agents. For example, the release characteristics of a particular bioactive and/or therapeutic agent may depend on its ability to diffuse from a particular matrix polymer. Thus, different compositions of matrix polymer and bioactive and/or therapeutic agent may provide different release characteristics therefrom. Some compositions may result in relatively fast release while others may result in a relatively slower release profile. By appropriate selection and arrangement of distinct layers of matrix polymer containing bioactive and/or therapeutic agents, the release profile of the different bioactive and/or therapeutic agent from the device may be optimized for a particular application.

For example, in one embodiment of the present invention adapted to provide controlled release of a bioactive and any optional therapeutic agents, there is provided a multilayer structure comprising a first annular layer comprising a biocompatible matrix polymer, an antimicrobial agent, a microbial attachment/biofilm synthesis inhibitor and, optionally, a therapeutic agent. First and second barrier layers (also annular in shape) are disposed on the exterior and interior surfaces, respectively, of the first annular layer. The first and second barrier layers that enclose the first annular layer are typically less permeable than the biocompatible matrix polymer and, thereby, control the rate of diffusion of the bioactive and optional therapeutic agents from the device to the external environment.

A simplified schematic representation of this embodiment of the present invention is depicted in FIG. 1. Implantable or insertable medical device 100 in accordance with this embodiment of the present invention comprises an annular first matrix polymer region 101; an annular first polymeric barrier layer 111 at least partially covering an interior surface of first matrix polymer region 101 and, an annular second polymeric barrier layer 112 at least partially covering an exterior surface of first matrix polymer region 101. Annular first and second polymeric barrier layers 111 and 112, respectively, may have the same or a different composition.

The barrier layers preferably comprise polymeric materials. Any of the non-biodegradable and biodegradable polymers described hereinabove in relation to the matrix polymer may also form a barrier layer. Preferred barrier layer polymers include, but are not limited to, ethylenic copolymers such as ethylene vinyl acetate and copolymers of ethylene with acrylic or methacrylic acid, elastomers including elastomeric polyurethanes and block and random copolymers thereof, metallocene catalyzed polyethylene (mPE) and mPE copolymers, ionomers, silicones and mixtures thereof. Metallocene catalyzed polyethylenes and mPE copolymers, such as copolymers of ethylene with octene, and ionomers and may be particularly preferred polymeric barrier layer materials to control partitioning of any bioactive agent such as salicylic acid or sodium salicylate to the surface of the matrix polymer during processing and to provide controlled release of active agents from the matrix polymer.

A barrier layer and any contacting matrix polymer layer or region will preferably comprise different polymeric materials. Different polymeric materials will generally provide different rates of diffusion or release of bioactive agent. Thus, less permeable barrier layers may be provided to control the rate of release of a bioactive agent from a contacting matrix polymer region which may be more permeable to diffusion of a bioactive agent. For example, where an EVA copolymer having a vinyl acetate content of from about 19% to about 28% is used as the matrix polymer, an EVA copolymer having a lower vinyl acetate content of from about 3% to about 15% may be useful to form the contacting barrier layer, or vice versa. The relative rigidity or stiffness of lower vinyl acetate content barrier layers may be offset somewhat where employed by the use of higher vinyl acetate content matrix polymer layers or regions, or vice versa. (Using triclosan as a specific example, the rate of release for triclosan is faster using stiffer or higher durometer EVA, and slower with lower durometer EVA.) While two barrier layers are provided in medical device 100 depicted in FIG. 1, it is understood that a medical device of the present invention may comprise an annular matrix polymer region provided with no barrier layer, or with a single barrier layer at least partially covering an exterior or interior surface of the annular matrix polymer region. It is also understood that while annular matrix polymer regions and annular barrier layers may be preferred in some embodiments of the present invention, neither any matrix polymer region nor any barrier layer need be annular.

In the medical device depicted in FIG. 1, and the above-described and other modifications thereof in accordance with the present invention, the first matrix polymer region preferably comprises a biocompatible matrix polymer as described herein, an antimicrobial agent, a microbial attachment biofilm synthesis inhibitor and, as further optional components, one or more of a radio-opacifying agent and a therapeutic agent.

Another embodiment of the present invention comprising a multi-layer structure will now be described. In this embodiment, the device is designed to provide slower release of a bioactive and/or therapeutic agent from a first matrix polymer composition relative to release of a bioactive and/or therapeutic agent from a second matrix polymer composition. In this embodiment, there is provided an annular layer of the first matrix polymer composition between distinct annular layers of the second matrix polymer composition. In such a multi-layer configuration, each surface of the second matrix polymer composition that would otherwise be exposed to the external environment is provided with a barrier layer. Similarly, barrier layers are provided between the annular layer of the first matrix polymer composition and the annular layers of the second matrix polymer composition. The resulting structure comprises seven layers, three of which form distinct matrix polymer regions and four of which form barrier layers covering at least a portion of one or more surfaces of the matrix polymer regions. In this configuration, the bioactive and/or therapeutic agent from the annular layer comprising the first matrix polymer composition would have to diffuse through its own barrier layer, into and through an annular layer comprising the second matrix polymer composition and through another barrier layer before reaching the external environment. This multi-layer configuration provides a slower release of bioactive and/or therapeutic agent from the annular layer of the first matrix polymer composition relative to the rate of release of bioactive and/or therapeutic agent from the annular layer of the second matrix polymer composition.

Figure 2:
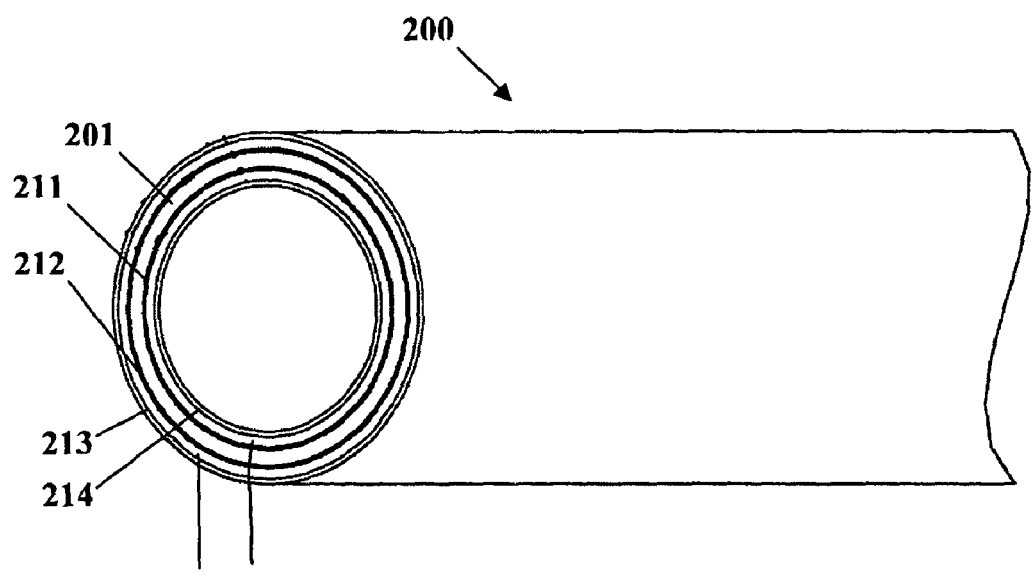
FIG. 2 is a simplified schematic representation (perspective view) of a portion of an implantable or insertable medical device in accordance with an embodiment of the present invention.

A simplified schematic representation of this embodiment of the present invention is depicted in FIG. 2. Implantable or insertable medical device 200 in accordance with this embodiment of the present invention comprises annular first matrix polymer region 201; annular first polymeric barrier layer 211 at least partially covering an interior surface of first matrix polymer region 201; annular second polymeric barrier layer 212 at least partially covering an exterior surface of first matrix polymer region 201; annular second matrix polymer region 202 at least partially covering an exterior surface of annular second polymeric barrier layer 212; annular third polymeric barrier layer 213 at least partially covering an exterior surface of annular second matrix polymer region 202; annular third matrix polymer region 203 disposed on an interior surface of annular first polymeric barrier layer 211; and annular fourth polymer barrier layer 214 at least partially covering an interior surface of annular third matrix polymer region 203.

Annular first, second, and third matrix polymer regions 201, 202 and 203, respectively, may have the same or different compositions. In a preferred embodiment, annular second and third matrix polymer regions 202 and 203, respectively, have the same composition which is different from the composition of annular first matrix polymer region 201. In this preferred embodiment, it is also preferred that annular first and second polymeric barrier layers 211 and 212, respectively, have the same composition and annular third and fourth polymer barrier layers 213 and 214, respectively, have the same composition. In this embodiment, it is particularly preferred that the annular first and second polymeric barrier layers 211 and 212, respectively, have a composition different from that of the annular third and fourth polymeric barrier layers, 213 and 214, respectively. However, more broadly, annular first, second, third and fourth polymeric barrier layers 211, 212, 213 and 214, respectively, may have the same or different compositions. Similarly, annular first, second and third matrix polymer regions 201, 202 and 203, respectively may have the same or different compositions.

Another embodiment of the present invention may also be described with reference to FIG. 2. In this embodiment, the medical device has two matrix polymer regions and three polymeric barrier layers. This embodiment of the present invention may be envisioned by removing, from the medical device depicted in FIG. 2, annular third matrix polymer region 203 and annular fourth polymer barrier layer 214, thereby resulting in a five layer structure comprising two distinct matrix polymer regions (201, 202) and three polymeric barrier layers (211, 212, 213) at least partially covering one or more surfaces of the distinct matrix polymer regions.

It is understood that other configurations of barrier layers and matrix polymer regions are within the scope of the present invention. For example, again with reference to FIG. 2, a five layer structure within the scope of the present invention may be envisioned by removing annular third and fourth polymeric barrier layers, 213 and 214, respectively. In this embodiment, the resulting five layer structure will comprise three distinct matrix polymer regions (201, 202, 203) separated from each other by two barrier layers (211, 212) disposed on inner and outer surfaces of annular first matrix polymer region 201.

In the medical device depicted in FIG. 2, and the above-described and other modifications thereof in accordance with the present invention, any of the first, second and optional third matrix polymer regions preferably comprises a biocompatible matrix polymer as described herein and either or both of an antimicrobial agent and/or a microbial attachment biofilm synthesis inhibitor and, as further optional components, one or more of a radio-opacifying agent and a therapeutic agent.

The present invention is not to be construed as limited in any way by the simplified schematic representations of the embodiments of the present invention as depicted in FIG. 1 or 2. Thus, a medical device in accordance with the present invention can be a single layer or multilayer construction; may have one or multiple matrix polymer regions and may have none, one or multiple barrier layers. Moreover, neither any matrix polymer region nor any barrier layer need be annular as depicted in the Figures. Further, where a barrier or other layer is provided in addition to a matrix polymer layer, any of a bioactive agent, a radio-opacifying agent and a therapeutic agent may be provided in or on such barrier or other layer.

Further optimization of release profiles can be obtained by providing a multilayer structure having both biodegradable and substantially non-biodegradable layers. Matrix polymer layers having different rates of biodegradation can, for example, provide different release profiles of bioactive and/or therapeutic agents. By appropriate selection and placement of such biodegradable layers, release profiles can be optimized based on the desired time-dependent requirements for release of such bioactive and/or therapeutic agents.

Multiple layers may also be provided to act as barrier layers to separate, at least temporarily, otherwise incompatible polymers, bioactive agents, therapeutic agents and radio-opacifying agents. For example, such materials or agents may not be compatible with another such material or agent under the processing conditions employed to manufacture the medical device. As a specific example, an antimicrobial agent such as chlorhexidine may react with a microbial attachment/biofilm synthesis inhibitor such as salicylic acid when mixed with an EVA copolymer under certain conditions in a twin screw extruder. The resultant chemical modification of the compounds may render them ineffective for their intended purpose. As another example, a radio-opacifying agent such as bismuth subcarbonate may react with an antimicrobial agent such as salicylic acid under certain processing conditions necessary for a particular matrix polymer.

The use of a barrier layer is also advantageous in substantially reducing or preventing the preferential partitioning of a bioactive agent to the surface of a medical device during or subsequent to processing. For example, a microbial attachment/biofilm synthesis inhibitor such as salicylic acid may preferentially partition to the surface of a matrix polymer such as an EVA copolymer during or subsequent to some of the processing steps involved in formation of the medical device. This preferential partitioning may be referred to as "blooming." It is believed that blooming may result, at least in part, when the bioactive agent has limited solubility in the polymer, particularly as it is cooled after processing. Also, a bioactive agent that has greater solubility in water than in a matrix polymer may be more susceptible to blooming during processing of the matrix polymer and bioactive agent. It may, therefore, be desirable to control moisture content during processing of the bioactive agent and matrix polymer to prevent blooming of bioactive agent. In any event, blooming may result in the appearance of crystals of the bioactive agent, such as salicylic acid, on the surface of the device within hours after processing.

In one embodiment of the present invention adapted to substantially reduce or prevent blooming, there is provided a multilayer structure comprising a first annular layer comprising a biocompatible matrix polymer, an antimicrobial agent, a microbial attachment/biofilm synthesis inhibitor; and annular first and second barrier layers on the exterior and interior surfaces, respectively, of the first annular layer (as optional components, a radio-opacifying agent and/or a therapeutic agent may also be added to one or more of the layers). Blooming or partitioning of a bioactive agent to a surface of the device can be effectively controlled by providing the first and second annular barrier layers in this embodiment. A medical device in accordance with this embodiment comprising a three layer structure adapted to substantially reduce blooming may have a structure similar to that shown in FIG. 1, described hereinabove.

In another aspect, the present invention is directed to a method of manufacturing an implantable or insertable medical device comprising (a) providing one or more biocompatible matrix polymers, one or more antimicrobial agents and/or one or more microbial attachment/biofilm synthesis inhibitors and, optionally, one or more of a radio-opacifying agent and/or a therapeutic agent; (b) processing the one or more biocompatible matrix polymers and the one or more bioactive agents, preferably under conditions that substantially prevent preferential partitioning of any of the bioactive agents to a surface of any of the biocompatible matrix polymers and that substantially prevent chemical modification of the one or more bioactive agents.

Processing typically comprises dry blending, mixing or compounding the matrix polymer, one or more bioactive agents, and further optional radio-opacifying and/or therapeutic agents to form a more homogeneous mixture thereof and shaping the homogenous mixture into a matrix polymer region of an implantable or insertable medical device. The mixing and shaping operations, as described more fully below, may be performed using any of the conventional devices known in the art for such purposes. In the following description, the one or more bioactive agents and further optional radio-opacifying and/or therapeutic agents will, at times, be collectively referred to as "additives" or "agents."

During processing, there exists the potential for one of more of the polymer matrix material, one or more bioactive agents and further optional radio-opacifying and/or therapeutic agents to become chemically modified by cross-reacting with one another. These undesirable cross-reactions may result from the incompatibility or instability of these agents at the elevated temperatures typically involved during the processing. It is also believed that excessive moisture content during processing may facilitate chemical modification of the agents.

Excessive moisture content can also facilitate blooming of a bioactive agent to a surface of a matrix polymer. Other processing conditions can also result, as discussed hereinabove, in blooming of one or more of the bioactive agents to the surface of a matrix polymer during and/or subsequent to processing.

Hence, processing is preferably performed under conditions that substantially prevent preferential partitioning of any of the agents and substantially prevent chemical modification of the agents. It is understood that some partitioning and chemical modification may be unavoidable during processing. Therefore, by "substantially prevent" is meant that no more than about 25% by weight, preferably less than about 10% by weight (based on the weight of the matrix polymer composition), of any bioactive agent is preferentially partitioned to a surface of a matrix polymer and/or chemically modified during processing.

Among the processing conditions that may be controlled during processing to substantially reduce the risk of partitioning and/or chemical modification are the temperature, moisture content, applied shear rate and residence time of the mixture of matrix polymer, one or more bioactive agents, and further optional radio-opacifying and/or therapeutic agents in a processing device.

Mixing or compounding a matrix polymer with one or more of the bioactive agents and further optional radio-opacifying and/or therapeutic agents to form a homogeneous mixture thereof may be performed with any device known in the art and conventionally used for mixing polymeric materials with additives. Where thermoplastic materials are employed, a polymer melt is formed by heating the various agents, which can then be mixed to form a more homogenous mixture. A common way of doing so is to apply mechanical shear to a mixture of the matrix polymer and additives. Devices in which the matrix polymer and additives may be mixed in this fashion include, but are not limited to, devices such as a single screw extruder, a twin screw extruder, a banbury mixer, a high-speed mixer, and a ross kettle.

Mixing may also be achieved by dissolving the matrix polymer with one or more of the bioactive agents and further optional radio-opacifying and/or therapeutic agents in a solvent system or forming a liquid dispersion of the same.

Any of the matrix polymer and/or additives may be pre-compounded or individually premixed to facilitate subsequent processing. For example, a radio-opacifying agent may be precompounded with a matrix polymer and then mixed with any bioactive agent. Alternatively, the radio-opacifying agent such as bismuth subcarbonate may be preblended with any bioactive agent in a device such as a v-mixer with an intensifier bar before being mixed with the matrix polymer.

In some preferred embodiments, a more homogenous mixture of the matrix polymer and additives is produced using a twin screw extruder, such as a twin screw extruder with a low-shear profile design. Barrel temperature, screw speed and throughput are typically controlled to prevent partitioning and chemical modification as discussed hereinabove.

The conditions necessary to achieve a more homogenous mixture of the matrix polymer and additives during compounding will depend, to some extent, on the specific matrix polymer as well as the type of mixing device used. For example, different matrix polymers will typically soften into a melt to facilitate mixing at different temperatures. It is generally preferred in some embodiments to mix the matrix polymer and additives at a temperature from about 60° C. to about 140° C., more preferably from about 70° C. to about 100° C., most preferably from about 80° C. to about 90° C. These temperature ranges have been found to result in formation of a more homogenous mixture of the matrix polymer and additives, while substantially preventing partitioning and chemical modification. Some combinations of matrix polymer and additive can be processed at a lower temperature than might otherwise be expected to result in homogeneous mixing. For example, while 70° C. may be a relatively low temperature for processing an EVA copolymer and an additive, an antimicrobial agent such as triclosan, which melts at a temperature of around 50° C., may act as a plasticizer for the EVA, facilitating use of a lower temperature of about 70° C. The ability to process the EVA at a lower temperature by virtue of an additive acting as a plasticizer advantageously reduces the risk of chemical modification of the additives if a higher temperature were otherwise required. Higher temperatures may be employed, however, during subsequent shaping of the homogenous mixture into a portion of a medical device as described herein. For example, higher temperatures may be necessary in localized portions of a coextrusion device used to apply a barrier layer onto one or more surfaces of the matrix polymer. However, the time at which the higher temperatures are encountered by the mixture are generally kept to a minimum.

The mixture of matrix polymer and additives can be shaped into at least a portion of a medical device in accordance with the present invention by means of any process conventionally used to shape polymeric materials such as thermoplastic and elastomeric materials. Among such shaping processes are included, but not limited to, extrusion including coextrusion, molding, calendaring, casting and coating. Among preferred shaping processes are extrusion and coextrusion processes.

Coextrusion is a particularly preferred shaping process wherein at least a portion of a medical device in accordance with the present invention is a multilayer structure, for example, comprising one or more distinct matrix polymer regions and one or more barrier layers at least partially covering a surface of a matrix polymer region. Among preferred coextruded multilayer structures are those having 3 to 7 distinct layers as described hereinabove. Especially preferred coextruded structures are those in which each of the matrix polymer regions and contacting barriers layers have annular shapes. For example, a three layer structure may be formed by coextruding annular polymeric barrier layers with an annular matrix polymer region such that the polymeric barrier layers at least partially cover interior and exterior surfaces of the matrix polymer region. Two, five, and seven layer constructions as described herein may be similarly formed by coextrusion, as can any multilayer construction having from 2 to about 50 layers. It is also understood that a medical device of the present invention may be formed by extruding a single annular matrix polymer containing one or more bioactive agents, an optional radio-opacifying agent and an optional therapeutic agent. Multi-layer structures can also be formed by other processing and shaping techniques such as laminar injection molding (LIM) technology. Alternatively, co-extrusion may comprise two mixtures of different polymer matrix with or without additives, wherein, for example, the mixtures are extruded according to a gradient such that the resultant medical device has sections with differing percentages of the mixtures ranging from 0-100%. For example, mixtures having a polymer matrix with a different durometer value may be extruded according to a gradient from 0%-100% to form a device, such as a stent, with opposing end regions having 100% of the respective mixtures and a transition region in between that is a co-extrusion of the two mixtures going from 100% of the one mixture at one end of the transition region to 100% of the other mixture at the other end of the transition region. Other lengthwise co-extrusions are contemplated to form sections along the length of a medical device that have different polymer matrices and/or different bioactive agents.

The temperatures used for shaping the matrix polymer and any barrier layers will, of course, depend on the particular materials used and the shaping device employed. Shaping process conditions, as with the mixing or compounding process conditions, may also result in undesirable partitioning and/or cross-reactions. Therefore, control of any shaping process condition such as temperature, moisture content, shear rate and residence time may be desirable to avoid partitioning and/or cross-reactions.

For example, a three layer structure comprising an annular matrix polymer region and two barrier layers covering an interior and exterior surface, respectively, of the matrix polymer region may be formed by coextruding the matrix polymer containing the one or more bioactive agents and further optional radio-opacifying agent and/or therapeutic agent. In such a coextrusion process, the barrel and shaping die temperatures, screw speed and compression ratio, may be controlled to prevent undesirable partitioning and chemical modification of the one or more bioactive agents. For example, coextrusion of a 19% vinyl acetate EVA copolymer as a matrix polymer, compounded with 10% by weight triclosan, 10% by weight salicylic acid and 30% by weight bismuth subcarbonate may be coextruded with two layers of a metallocene catalyzed polyethylene ("mPE") copolymer such as an ethylene-octene copolymer (24% octene co-monomer) serving as barrier layers. In such a coextrusion process, a screw speed of 35 rpm on a 3:1 compression ratio, using a 1" screw diameter with no mixing section and a barrel temperature of about 110° C. was found to be sufficient to substantially prevent cross-reactions and bioactive agent partitioning. As alluded to above, barrier layer materials may require higher processing temperatures during shaping than temperatures employed during compounding of the matrix polymer and additives. Consequently, it may be necessary to maintain portions of the extrusion apparatus at higher temperatures than employed during compounding. In this embodiment, a barrel temperature of about 110° C. and a shaping head temperature of about 150° C. are employed to facilitate formation of the mPE copolymer barrier layers. While these temperatures are higher than the temperature (about 70° C.) used to compound the EVA matrix polymer and additives, substantial partitioning and chemical modification of the bioactive agents may, nonetheless, be avoided, due in part to the short residence time at these temperatures.

Other shaping processes, as mentioned above, include extrusion coating and solvent coating. For example, a barrier layer polymer could be extruded onto a preformed matrix polymer region. This process is distinguished from a coextrusion process in which the matrix polymer and barrier layers are shaped substantially simultaneously. Alternatively, a barrier layer could be applied to a surface of a matrix polymer by applying a solvent solution or liquid dispersion of a barrier polymer onto a surface of the matrix polymer followed by removing the solvent or liquid dispersing agent, e.g., by evaporation. Such a solution or dispersion of the barrier polymer may be applied by contacting a surface of the matrix polymer with the solution or dispersion by, for example, dipping or spraying. The use of these other shaping processes is not limited to the application of a barrier layer to a matrix polymer region. Therefore, a matrix polymer region may also be formed onto a preformed substrate by similar methods.

The medical device of the present invention may be any implantable or insertable medical device, particularly one that may be susceptible to microbial growth on and around the surfaces of the device, including attachment of microbes onto and the synthesis by attached microbes of biofilm on the surface of the medical device. Preferred implantable medical devices include those adapted to remain implanted for a relatively long-term, i.e., for period of from about 30 days to about 12 months or greater. However, devices intended to remain implanted for about 30 days or less are also included within the scope of the present invention.

Examples of implantable medical devices include, but are not limited to, stents, stent grafts, stent covers, catheters, artificial heart valves and heart valve scaffolds, venous access devices, vena cava filters, peritoneal access devices, and enteral feeding devices used in percutaneous endoscopic gastronomy, prosthetic joints and artificial ligaments and tendons. Preferred medical devices include those adapted to bridge or provide drainage between two sterile areas of the body or between a sterile and non-sterile area of the body. Devices adapted to bridge or provide drainage between a sterile and a non-sterile area of the body are particularly susceptible to microbial growth, attachment and biofilm formation due to contamination of the sterile area from microbes normally present in the non-sterile area. Medical devices intended to be implanted in or bridge sterile body environments may be susceptible to microbial growth, attachment and biofilm formation, for example, from microbial organisms that are ordinarily present in the non-sterile area (i.e., non-pathogenic organisms), from those that are present due to disease, (i.e., pathogenic organisms) and from those introduced during the insertion or implantation of the medical device.

Stents include biliary, urethral, ureteral, tracheal, coronary, gastrointestinal and esophageal stents. Preferred stents include biliary stents, ureteral stents and pancreatic stents. The stents may be of any shape or configuration. The stents may comprise a hollow tubular structure which is particularly useful in providing flow or drainage through biliary and ureteral lumens. Stents may also be coiled or patterned as a braided or woven open network of fibers or filaments or, for example, as an interconnecting open network of articulable segments. Such stent designs may be more particularly suitable for maintaining the patency of a body lumen such as a coronary artery. Thus, stents adapted primarily to provide drainage, in contrast to stents adapted primarily to support a body lumen, will preferably have a continuous wall structure in contrast to an open network wall structure.

Stent covers are also a preferred medical device of the present invention. For example, a stent cover may comprise a thin wall tubular or sheath-like structure adapted to be placed over a stent comprising an open mesh stent of knitted, woven or braided design. A preferred stent cover is adapted to be placed over a biliary stent. The biliary stent can be made of any material useful for such purpose including metallic and non-metallic materials as well as shape memory materials. Among useful metallic materials include, but are not limited to, shape memory alloys such as Nitinol®, and other metallic materials including, but not limited to, stainless steel, tantalum, nickel-chrome, or cobalt-chromium, i.e., Elgiloy®. The biliary stent can be made from a single strand or multiple strands of any such material and may be self-expanding. The stent cover may comprise, for example, a matrix polymer as described herein which comprises an antimicrobial agent such as triclosan, a microbial attachment/biofilm synthesis inhibitor such as salicylic acid and a radio-opacifying agent such as bismuth subcarbonate. A particularly preferred stent cover comprises an elastomeric polyurethane or polyurethane copolymer as described above. The stent cover is particularly advantageous in reducing tissue growth through an open mesh stent while at the same time reducing microbial growth on and around the surface of the stent, reducing attachment of microbes onto the stent, and reducing the synthesis of biofilm on the surface of the stent.

Another preferred medical device of the present invention is a pancreatic stent that provides drainage from the pancreas to the duodenom. Normally, the pancreas drains into the duodenum by the pancreatic duct. Implantable pancreatic drainage devices are sometimes desired to alleviate problems such as strictures, sphincter stenoses, obstructing stones or to seal duct disruptions. However, when the pancreatic duct is opened, or an implantable medical device is placed in the pancreas, morphological changes may occur that may lead to pancreatitis.

It is believed that morphological changes in the pancreas upon insertion of an implantable medical device may be related to the pH difference between a normal pancreas and the duodenum into which the pancreas drains. The pancreas has a higher pH than the duodenum and excretes aqueous bicarbonate to buffer the duodenum. The implantation of a medical device into the pancreas may substantially reduce the ability or effectiveness of the pancreas to provide this buffering action, potentially leading to undesirable morphological changes in the pancreas.

It is believed that by providing a pancreatic stent that releases a buffering agent so as to create a pancreatic pH level in the environment of the implanted medical device, undesirable morphological changes in the pancreas may be substantially reduced or even prevented. This may be accomplished by providing an agent in or on the surfaces of a pancreatic stent such that when the pancreatic stent is exposed to physiological fluids, the buffering agent is released from the stent creating a locally higher pH environment around the device. Among buffering agents are included, but not limited to, bicarbonate salts such as sodium or potassium bicarbonate. Such buffering agents may be incorporated, for example, in a matrix polymer in a manner described hereinabove with respect to bioactive agents, or they may be applied as a coating on a surface of a matrix polymer, or they may be applied in or as a coating on any optional barrier layer by any of the methods described above.

The invention will be further described with reference to the following non-limiting Examples. It will be apparent to those skilled in the art that many changes can be made in the embodiments described in such Examples, consistent with the foregoing description, without departing from the scope of the present invention.

Example 1

A single-layer matrix polymer structure is formed from a mixture containing an ethylene vinyl acetate (EVA) copolymer having a 19% vinyl acetate content, 10% triclosan by weight of the mixture as an antimicrobial agent, 10% salicylic acid by weight of the mixture as a microbial attachment/biofilm synthesis inhibitor, and 30% bismuth subcarbonate by weight of the mixture as a radio-opacifying agent. The bismuth subcarbonate is precompounded with the EVA copolymer (62.5% EVA/37.5% bismuth subcarbonate) and added to the triclosan and salicylic acid bioactive agents. Alternatively, the bismuth subcarbonate is preblended with the triclosan and salicylic acid in a v-mixer with intensifier bar before adding to the polymer. A v-blender with an approximately 13 rpm shell speed and a pin-type intensifier bar at about 120 rpm for about 15 minutes produces a consistent, homogenous powder blend. The triclosan, salicylic acid and bismuth subcarbonate are compounded with the EVA copolymer in an 18 mm screw diameter twin screw extruder with a low-shear profile screw design. The barrel temperature in the screw is about 70° C. with a screw speed of about 200 rpm and a throughput of about 3.5 kg/hr. Since 70° C. is a relatively low processing temperature for EVA, the triclosan acts as a plasticizer to facilitate compounding and subsequent extrusion. After compounding, the mixture is extruded into tubes in a standard 1" screw diameter extruder with a 24:1 L/D, 3:1 compression ratio, low shear screw. Maximum barrel temperature is about 100° C. to prevent reaction between the bismuth subcarbonate and the salicylic acid. The screw speed is kept relatively low, around 20 rpm, to keep the shear rate low and prevent excess viscous heat dissipation.

Example 2

A three-layer structure is formed having a matrix polymer region with the same composition and compounding as described in Example 1, and coextruded with barrier layers covering the inner and outer surfaces of the matrix polymer region. The barrier layers are formed of an ethylene-octene copolymer in which the octane co-monomer content is about 24%. Each of the barrier layers forms about 5% of the total wall thickness of the three-layer structure. Thicker or thinner barrier layers may be provided to retard or increase the release rate of the bioactive agents from the matrix polymer. The compounded matrix polymer and barrier layers are coextruded while controlling the screw speed and temperature to avoid overheating and undesirable cross-reactions and the consequent chemical modification of the bioactive agents and/or radio-opacifying agent. The coextrusion is performed using a screw speed of about 35 rpm on a 3:1 compression ratio, a 1" diameter screw with no mixing section. A barrel temperature of about 110° C. was found to substantially prevent cross-reactions. The copolymer barrier layers require higher processing temperatures at the shaping die at the head of the extruder. A shaping die temperature of about 150° C. was found to provide adequate head pressure, layer quality and cross-reaction at the shaping die.

Example 3

Approximately 2 cm lengths of extruded 19% vinyl acetate EVA copolymer tubing containing varying amounts of triclosan (TCN), salicylic acid (SA) and bismuth subcarbonate (BsC) are incubated in phosphate buffered saline (PBS) at 37° C. for 0 ("no treatment"), 3, 8 and 28 days. The purpose of incubation in PBS is to show longevity of SA inhibition on bacterial attachment after exposure, and release of SA from the extruded tube. After incubation in PBS, the tubes are exposed a solution containing approximately $10^{-4}$ to $10^{-5}$ cfu/ml $e.$ $coli$ for about 4 hr at 37° C. with rotation at about 100 rpm. Subsequent to this exposure, the samples are rinsed in saline and "rolled" following an established pattern onto a standard Mueller-Hinton agar plate. The plates are incubated for about 18 to 24 hr to allow colonies to form. The colonies are counted and expressed as cfu per inch of tube.

Figure 3:
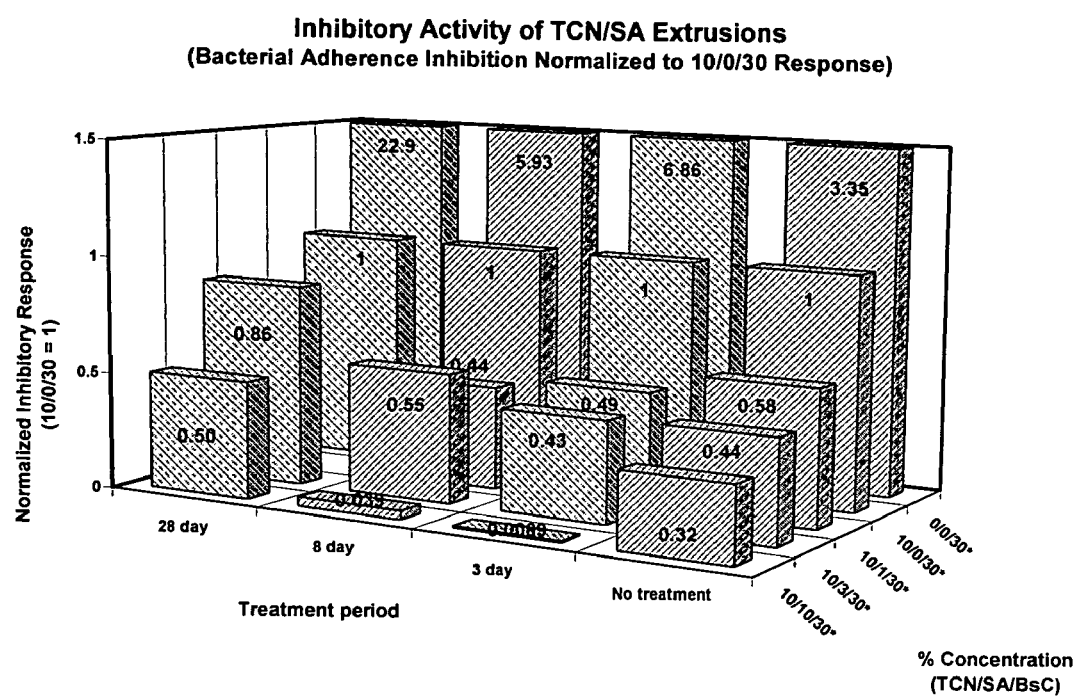
FIG. 3 is a graph showing bacterial attachment inhibition onto extruded tubes containing varying amounts of triclosan (TCN) and salicylic acid (SA).
Figure 4:
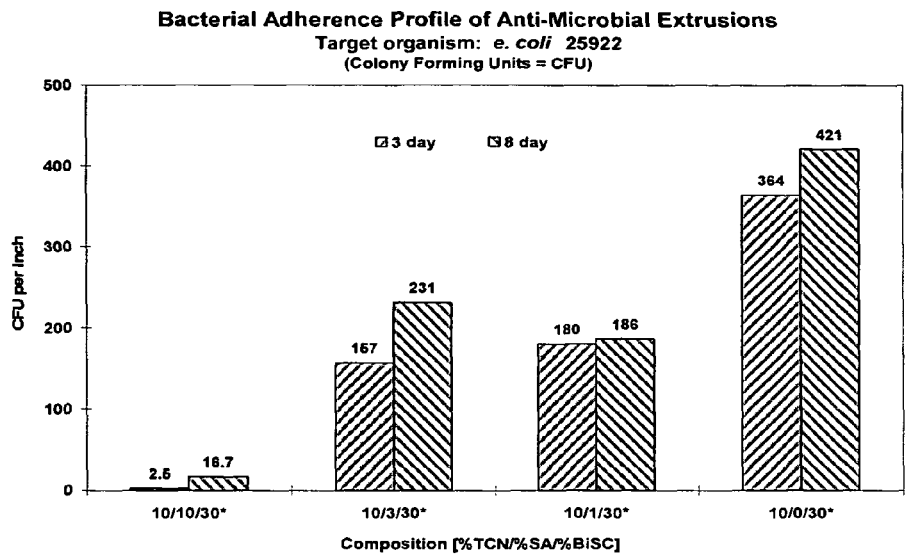
FIG. 4 is a graph showing bacterial attachment inhibition onto extruded tubes containing varying amounts of triclosan (TCN) and salicylic acid (SA).

FIG. 3 shows the normalized inhibitory response of the tubes. The amounts of TCN, SA and BsC in the tubes are represented as % TCN/% SA/% BsC (wt % based on weight of vinyl acetate EVA copolymer). Therefore, a tube having 10% TCN, 0% SA and 30% BsC is designated in FIG. 3 as "10/0/30". FIG. 3 shows the inhibitory response of five tubes having varying weight percentages of TCN and SA and 30% BsC, normalized to a 10/0/30 tube, given an inhibitory response value of 1. FIG. 3 shows that tubes containing 10% TCN and varying amounts (1%, 3% and 10% SA) inhibited bacterial attachment more effectively than tubes containing only TCN ("10/0/30") and inhibited bacterial attachment more effectively than tubes containing neither TCN nor SA ("0/0/30"). FIG. 3 also shows that, as the amount of SA increased from 0% to 10%, with TCN constant at 10%, the tubes were generally more effective at inhibiting bacterial attachment, suggesting that SA provides a synergistic effect. FIG. 3 further shows that incubation of the tubes in PBS prior to exposure to $e.$ $coli$ did not significantly affect bacterial inhibition, suggesting that effective amounts of TCN and SA remained in the extruded tubes after extended incubation in PBS, i.e., that the bioactive agents were not excessively or prematurely leached out of the extruded tubes. FIG. 4 shows results (not normalized) for similar tubes incubated for 3 and 8 days in PBS prior to exposure to $e.$ $coli$.

Example 4

Figure 5:
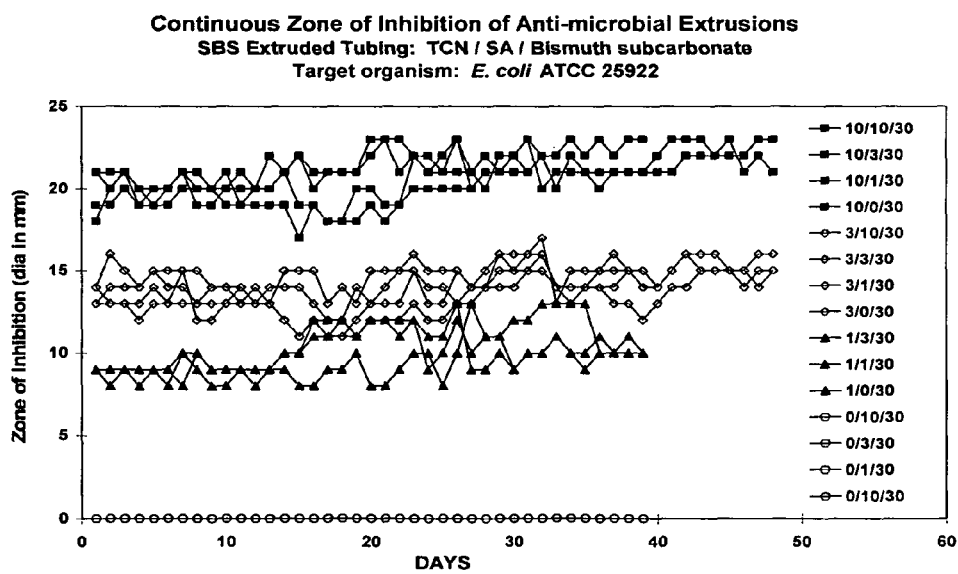
FIG. 5 is a graph showing the zone of bacterial (*E. coli* ATCC 25922) growth inhibition around extruded tubes containing varying amounts of triclosan (TCN) and salicylic acid (SA).
Figure 6:
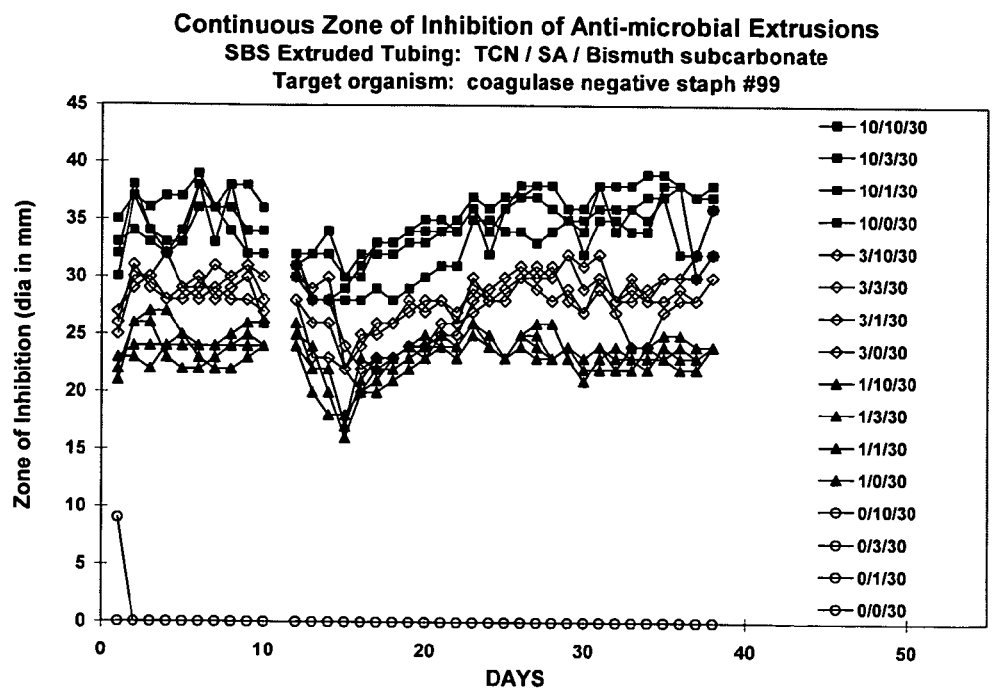
FIG. 6 is a graph showing the zone of bacterial (coagulase negative staph #99) growth inhibition around extruded tubes containing varying amount of triclosan and salicylic acid (SA).

Approximately 2 cm lengths of extruded 19% vinyl acetate EVA copolymer tubing containing varying amounts of triclosan (TCN), salicylic acid (SA) and bismuth subcarbonate (BsC) are inserted into an agar lawn of either $e.$ $coli$ (FIG. 5) or staph (FIG. 6). The tubes are positioned so as to extend vertically upwardly from the surface of the agar lawn (similar to birthday candles). After 24 hours in the agar lawn, the zone (diameter) of bacterial growth inhibition around the tubes is measured. The tubes are repositioned in fresh agar plates every 24 hours, and the zone of bacterial growth inhibition is again measured. FIG. 5 shows the measurement results for the tubes positioned in the agar lawn of *e. coli* and FIG. 6 shows the results for the tubes positioned in the agar lawn of staph. FIGS. 5 and 6 show that the zone of bacterial growth inhibition was larger as the percentage of TCN increased from 0% to a maximum of 10%. A tube containing no TCN, but varying amounts of SA did not effectively inhibit bacterial growth, suggesting that bacterial growth inhibition (as opposed to inhibition of bacterial attachment) is predominantly provided by TCN. FIGS. 5 and 6 also show that, for a given percentage of TCN, the measured zone of bacterial growth inhibition is similar over a period extending to about 40 days or longer, suggesting that the TCN component in the extruded tubes effectively maintains its activity for extended periods of time.

Example 5

Figure 12:
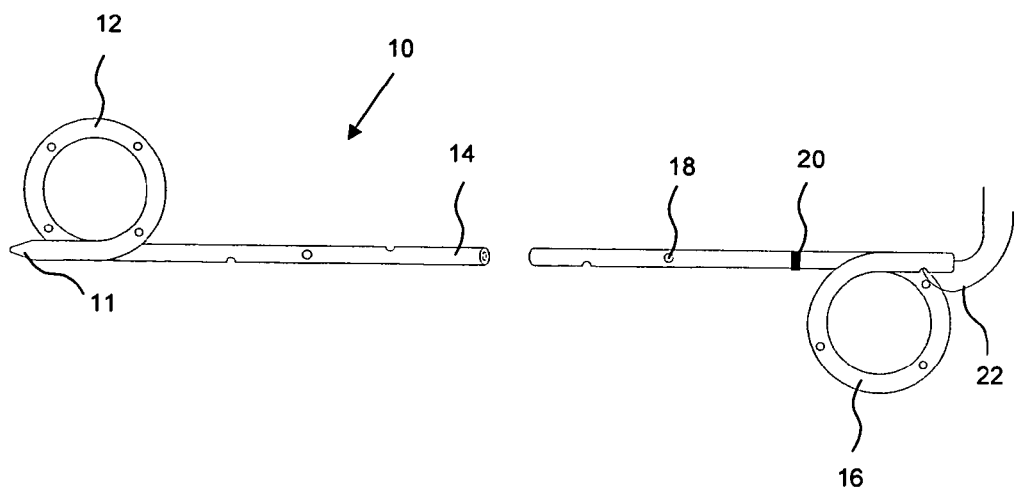
FIG. 12 is a ureteral stent for use in connection with the present invention.

Ureteral stents are used, for example, in post endourological procedures to act as a scaffold in the event of ureteral obstruction secondary to the procedure. Stents are also used as palliative devices to provide patency in the presence of congenital defects, strictures or malignancies that cause a ureter obstruction. The ureteral stents of the present Example are formed based on the design of the Percuflex® Ureteral Stent, which is commercially available from Boston Scientific, Natick, Mass., USA. A schematic diagram of such a stent 10 is illustrated in FIG. 12. The stent 10 is a tubular polymer extrusion containing a renal pigtail 12, a shaft 14 and a bladder pigtail 16. The stent 10 is inserted into the ureter to provide ureteral rigidity and allow the passage of urine. The pigtails 12, 16 serve to keep the stent 10 in place once positioned by the physician. The stent 10 is further provided with the following: (a) a tapered tip 11, to aid insertion, (b) multiple side ports 18 (one numbered), which are arranged in a spiral pattern down the length of the body to promote drainage, (c) graduation marks 20 (one illustrated), which are used for visualization by the physician to know when the appropriate length of stent has been inserted into the ureter, and (d) a Nylon suture 22, which aids in positioning and withdrawal of the stent, as is known in that art. During placement, such ureteral stents 10 are typically placed over a urology guidewire, through a cystoscope and advanced into position with a positioner. Once the proximal end of the stent is advanced into the kidney/renal calyx, the guidewire is removed, allowing the pigtails 12, 16 to form in the kidney and bladder.

Unlike the above Percuflex® Ureteral Stent, however, the stents used in the present Example contain triclosan. A nonionic, broad spectrum, antimicrobial agent, triclosan has been used for more than twenty years in a variety of personal care products such as shower gels, soaps, mouthwash and toothpaste, detergents, lotions, creams, and cosmetics. It is also incorporated into plastic toys, polymers, and textiles. Recently, triclosan has been incorporated as an antimicrobial agent in a biodegradable coated VICRYL Plus antimicrobial Suture from Ethicon, Inc., a Johnson & Johnson Company. The antimicrobial effectiveness of triclosan is well documented and described to be immediate, persistent and broad-spectrum against most gram positive and gram negative aerobic and anaerobic bacteria, some yeast and fungi, even at a very low concentration (MIC<0.3 ppm) in most organisms tested. See, Bhargava, H. N. PhD; Leonard, Patricia A. BS: Triclosan: Application and safety. AJIC American Journal of Infection Control, vol. 24(3) June 1996, pp 209-218; Jones R D, Jampani H B, Newman J L, Lee A S: Triclosan: a review of effectiveness and safety in health care settings. Am J Infect Control 2000 April; 28(2):184-96; Regos J, Zak O, Solf R., Vischer W A, Weirich E G: Antimicrobial spectrum of triclosan, a broad-spectrum antimicrobial agent for topical application. II. Comparison with some other antimicrobial agent. Dermatologia 1979; 158(1): 72-9.

The triclosan-containing ureteral stents contain the following ingredients in the following amounts: (a) either 12 wt % or 18 wt % triclosan (available under the trade name Irgacare™ MP from Ciba Specialty Chemicals), (b) 23 wt % bismuth subcarbonate (Mallinckrodt), (c) 0.45 wt % colorant, and (d) the balance ethylene vinyl acetate copolymer (Elvax 460, from DuPont). First, the triclosan, bismuth subcarbonate and colorant are preblended in a v-mixer with intensifier bar before adding to the polymer. A v-blender with an approximately 13 rpm shell speed and a pin-type intensifier bar at about 120 rpm for about 15 minutes produces a consistent, homogenous powder blend. The blended triclosan, bismuth subcarbonate and colorant are then compounded with the EVA copolymer in an 18 mm screw diameter twin screw extruder with a low-shear profile screw design. The barrel temperature in the screw is about 70° C. with a screw speed of about 200 rpm and a throughput of about 3.5 kg/hr. After compounding, pellets are extruded into tubes of an appropriate diameter in a standard 1" screw diameter extruder with a 24:1 L/D, 3:1 compression ratio, low shear screw at a screw speed of 20-35 rpm. Barrel temperature is 100-125° C. Although the compounding may not be 100% homogeneous, mixing the compounded pellets again before extrusion leads to a more uniform TCN loading.

The extruded material is then cut, provided with a tapered tip, annealing at 155° C. for 2 hrs, marked with ink (Formulab CFX-00) and coated with Hydroplus™ (Union Carbide, Dow Chemical) coating, followed by side port formation, pigtail formation by hot air treatment, and the addition of the suture, as is known in the art.

Example 6

Triclosan release tests are conducted by measuring flow-through release by the stent (i.e., a 6 French, 39 cm length stent, sterilized 1× in ethylene oxide (EtO)) into artificial urine (AU), such as that detailed in the British Standard for simulated/artificial urine formulation, at a flow rate of 0.5 ml/min. (Similar release results are obtained with 10 mM PBS.) For this purpose, the stent is placed inside a piece of tygon tubing which is connected to a peristaltic pump to deliver the AU media. The tubing and stent are submerged in a 37° C. water bath to simulate body temp. Release is measured over a period of 120 days and is presented as follows: in FIG. 7 as amount of triclosan released vs. days of urine exposure, in FIG. 8 as the concentration of triclosan vs. days of urine exposure, and in FIG. 9 as % of total triclosan released vs. days of urine exposure. As can be seen by referring to these figures, the stents exhibit a daily release rate of 675 μg/day (0.94 μg/ml effluent urine concentration) on the first day of release, and a 200 μg/day (0.27 μg/ml) release rate after 30 days exposure. Following 30 days, the release rate slowly drops to about 32 μg/day (0.04 μg/ml) post 90 days. The total amount of triclosan released during ninety days was about 16 mg, or 14% of the stent's total triclosan content. (Depending on the stent size, e.g., 5-8 FR, 20-30 cm, and assuming a triclosan concentration of 11±3 wt %, the overall triclosan content in the stent will generally range from about 100 to 240 mg.) These data show that the stents continue to release significant amounts of triclosan after long term (>90 days) urine exposure.

Figure 7:
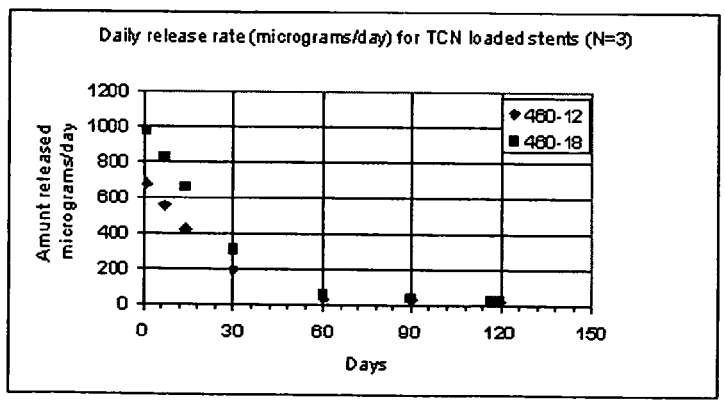
FIG. 7 is a graph showing the amount of triclosan released as a function of the number of days of urine exposure.
Figure 8:
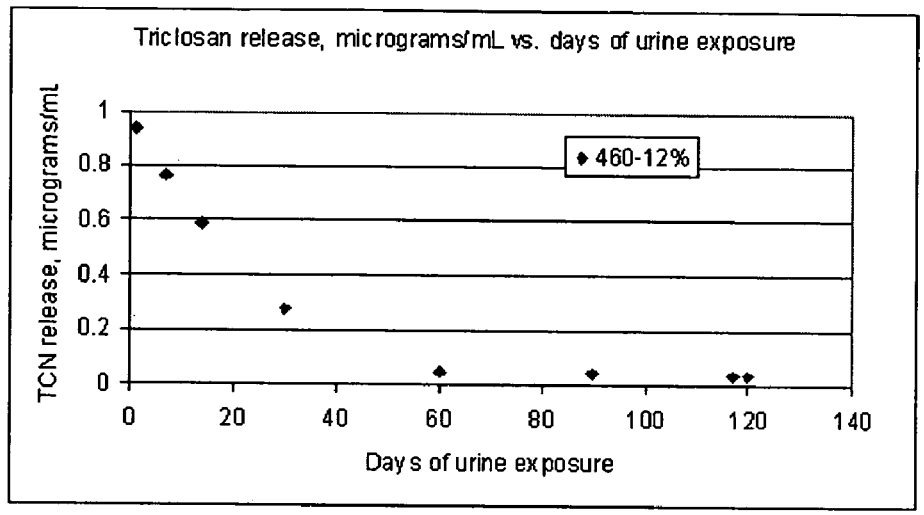
FIG. 8 is a graph showing the concentration of triclosan released as a function of the number of days of urine exposure.
Figure 9:
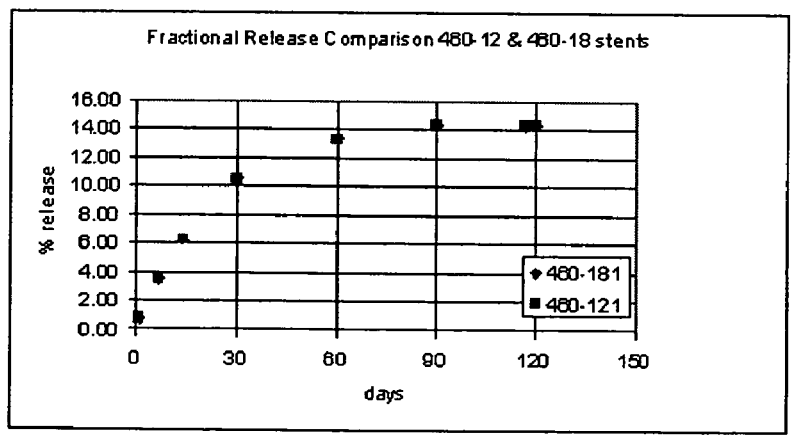
FIG. 9 is a graph showing the % of the total triclosan in the stent as a function of the number of days of urine exposure.

As seen in FIG. 7, an increase in total triclosan loading from 12% to 18% increased the first day release rate to 975 µg/day (1.4 µg/ml effluent urine concentration) with the release rate being reduced to about 36 µg/day (0.05 µg/ml) post 90 days. For 18% TCN, the total TCN loading is 175.9 mg and the amount released is 25.29 mg (for a % release of 14.38%). For 12% TCN loading, the TCN loading is 115.5 mg and the amount released is 16.66 mg (for a % release of 14.42%). Thus, while the absolute amount of the triclosan released at 12% and 18% loadings are different, the % of total triclosan released at any time point for both loadings are the same, as seen in FIG. 9. This indicates that the % of triclosan release was independent of the total initial loading of the stent. In general, however, as the drug-to-polymer ratio increases, the rate (or %) of TCN release is expected to increase as well. It is believed that this effect is not observable in this example, because the drug-polymer ratio is not sufficiently different and the difference between the amount of the TCN released and the total (e.g., ug vs mg) is very large.

Example 7

The most common issues related to the use of ureteral stents and other urinary tract medical devices are infection and encrustation. The microbial etiology of urinary infections has been regarded as well established and reasonably consistent. Most pathogens responsible for urinary tract infection are enterobacteriaceae of which *Escherichia coli* remains the most predominant uropathogen (80%). Other less common strains include *Proteus* (i.e. *Proteus mirabillis*), *Klebsiella* (i.e. *Klebsiella pneumoniae*), *Enterobacter* (i.e. *Enterobacter Cloacae*), *Enterococcus* (i.e. *Enterococcus faecalis*), *Pseudomonas* (i.e. *P. aeruginosa*) and *Candida* (i.e. *Candida albicans*) species as well as gram positive microbes such as *Staphylococcus epidermidis, Staphylococcus aureus* and *Staphylococcus saprophyticus*. The problem of encrustation of urinary catheters or stents stems from infection by *Proteus mirabilis* or other urease-producing bacteria. These organisms colonize device surfaces forming biofilm communities embedded in a polysaccharide matrix. Urease generates ammonia and raises the pH of urine. Under these conditions, crystals of magnesium and calcium phosphates form and lead to encrustation of the device. Thus, the selected test organisms for this Example and the Example to follow, *E. coli* and *Proteus mirabilis*, represent two of the most important pathogens for the clinical use of ureteral stents.

This Example evaluates the in vitro antimicrobial activity of ureteral stents (6Fr×39 cm, 1× EtO sterilized) containing 12% and 18% triclosan, which are exposed to synthetic urine flowing at the rate of 0.5 ml/min for >90 days. Test stents that were not exposed to urine served as positive controls. Stents that did not contain triclosan were used as negative controls. The antimicrobial activity of stents is assessed using a standard zone of inhibition test as described in Example 4 above, except that sample sections tested came from the flow-through study post >90 days, and they were only tested once at 24 hrs. Clinical isolates of *Proteus mirabilis* and *Escherichia coli* were used as test organisms.

Figure 10:
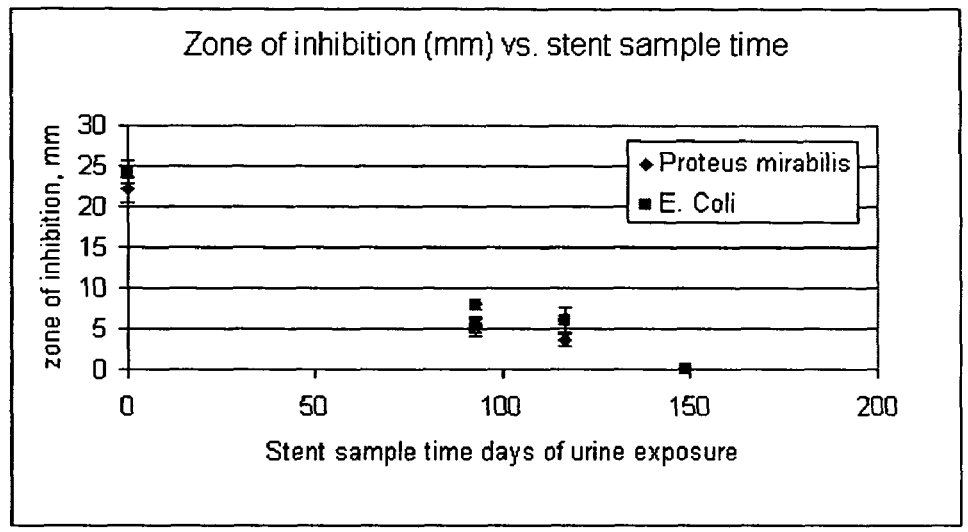
FIG. 10 is a graph showing zone of inhibition size as a function of triclosan release concentration.
Figure 11:
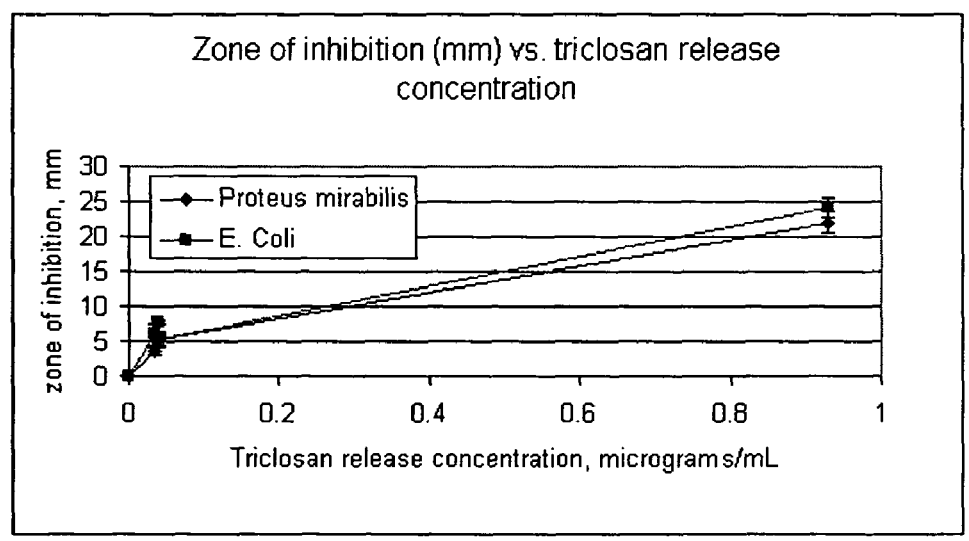
FIG. 11 is a graph showing zone of inhibition size as a function of triclosan release concentration in FIG. 11.

Zone of inhibition data are presented in FIG. 10 for stents with 12 wt % and 18 wt % TCN loads as a function of the concentration of triclosan released into the agar medium. It can be observed that the finished stent as a positive control exhibits a zone of inhibition>20 mm. As the stent is exposed to urine, and triclosan is released from the stent, this zone of inhibition decreases, yet is maintained to be >3.5 mm for stents after continuous exposure to artificial urine for 117 days. Zone of inhibition data are also presented in FIG. 11 as a function of triclosan release concentration.

Example 8

In this Example, the relative encrustation potential is assessed for several different stent configurations. A dynamic encrustation test (i.e., simulated clinical conditions) in artificial urine is conducted to determine the rate and extent of encrustation. A clinical isolate of *Proteus mirabilis* (ATCC, #25933) was used as test organism. All non-triclosan-containing stent types were observed to encrust after 6 days of exposure to inoculated and uninoculated AU (1× EtO sterilized). When visually assessed and when subjected to elemental analysis for magnesium and calcium, the triclosan-containing stents were not observed to encrust throughout the exposure period (15 days). Hence, incorporation of triclosan in the stents has the potential reduce encrustation and therefore preserves the patency of the stent.

The invention may be embodied in other specific forms without departing from its proper scope. The described embodiments and Examples are to be considered in all respects only as illustrative and not restrictive. The scope of the invention is, therefore, indicated by the appended claims rather than by the foregoing description. All changes that come within the meaning and range of equivalency of the claims are to be embraced within their scope.

What is claimed is:

1. A stent comprising
   (A) a polymeric tubular shaft having more than one layer, said polymeric tubular shaft comprising a first annular layer comprising an extruded homogenous mixture of a matrix polymer, an antimicrobial agent and a microbial attachment/biofilm synthesis inhibitor that form a single distinct matrix polymer region;
   (B) a first polymeric barrier layer at least partially covering an interior surface of said first annular layer; and
   (C) a second polymer barrier layer at least partially covering an exterior surface of said first annular layer.

2. The stent of claim 1, wherein said stent is a ureteral stent.

3. The stent of claim 1, wherein said antimicrobial agent comprises triclosan and said polymeric tubular shaft comprises between 5 and 20 wt % triclosan.

4. The stent of claim 1, wherein said matrix polymer is an ethylenic copolymer.

5. The stent of claim 1, wherein said matrix polymer is an ethylene vinyl acetate copolymer.

6. The stent of claim 5, wherein said polymeric tubular shaft comprises between 60 and 80 wt % of said ethylene vinyl acetate copolymer.

7. The stent of claim 5, wherein said ethylene vinyl acetate copolymer has a vinyl acetate content between 19 wt % and about 28 wt %.

8. The stent of claim 1, wherein said stent further comprises a lubricious hydrophilic coating on an outside surface of said polymeric tubular shaft.

9. The stent of claim 1, wherein said polymeric tubular shaft comprises a plurality of apertures formed in the walls of the same.

10. The stent of claim 1, wherein said polymeric tubular shaft further comprises a radio-opacifying agent.

11. The stent of claim 10, wherein said radio-opacifying agent is bismuth subcarbonate.

12. The stent of claim 1, wherein said polymeric tubular shaft is a melt-extruded tubular shaft.

13. The stent of claim 1, wherein said polymeric tubular shaft has a wall thickness ranging from 0.2 mm to 0.8 mm.

14. The stent of claim 1, wherein said polymeric tubular shaft comprises end regions of different durometer value.

15. A ureteral stent comprising
(A) a polymeric tubular shaft that is between 0.2 mm and 0.8 mm in wall thickness, said polymeric tubular shaft having more than one layer and comprising a first annular layer comprising an extruded homogenous mixture of a matrix polymer and a bioactive agent that form a single distinct matrix polymer region wherein:
  (a) polymeric species of the matrix polymer consists essentially of ethylene vinyl acetate copolymer; and
  (b) the bioactive agent consists essentially of triclosan;
(B) a first polymeric barrier layer at least partially covering an interior surface of said first annular layer; and
(C) a second polymer barrier layer at least partially covering an exterior surface of said first annular layer.

16. The ureteral stent of claim 15, further comprises a radio-opacifying agent.

17. The ureteral stent of claim 15, further comprising a lubricious hydrophilic coating on an outside surface of said polymeric tubular shaft.

18. The ureteral stent of claim 15, wherein said polymeric tubular shaft is a melt-extruded polymeric tubular shaft.

19. The ureteral stent of claim 15, wherein between 5 and 15% of the total triclosan in the stent is released after 30 days exposure to synthetic urine at a flow rate of 0.5 ml/min, and between 10 and 20% of the total triclosan in the stent is released after 90 days exposure to synthetic urine at a flow rate of 0.5 ml/min.

20. The ureteral stent of claim 15, wherein between 20 μg and 50 μg per day of triclosan is released after 90 days exposure to synthetic urine at a flow rate of 0.5 ml/min.

21. The ureteral stent of claim 15, wherein between 100 μg and 500 μg per day of triclosan is released after 30 days exposure to synthetic urine at a flow rate of 0.5 ml/min.

22. The ureteral stent of claim 15, wherein said polymeric tubular shaft comprises end regions of different durometer value.

23. The stent of claim 1, wherein the microbial attachment/biofilm synthesis inhibitor comprises a non-steroidal anti-inflammatory drug or a chelating agent.

24. The stent of claim 1, wherein the microbial attachment/biofilm synthesis inhibitor comprises a chelating agent selected from the group consisting of EDTA, EGTA and mixtures thereof.

25. The stent of claim 1, wherein the microbial attachment/biofilm synthesis inhibitor comprises a mixture of a non-steroidal anti-inflammatory drug and a chelating agent.

26. The stent of claim 23, wherein the non-steroidal anti-inflammatory drug comprises: salicylic acid or its derivatives or an acrylcarboxylic acid selected from the group consisting of clidanac, ketorolac, tinoridine and a salt or derivative thereof; and the chelating agent is selected from the group consisting of EDTA, EGTA and a mixture of EDTA and EGTA.

27. The stent of claim 25, wherein the non-steroidal anti-inflammatory drug comprises: salicylic acid or its derivatives or an acrylcarboxylic acid selected from the group consisting of clidanac, ketorolac, tinoridine and a salt or derivative thereof; and the chelating agent is selected from the group consisting of EDTA, EGTA and a mixture of EDTA and EGTA.

28. The stent of claim 1, wherein the stent further comprises a radio-opacifying agent comprising bismuth subcarbonate, and the stent further comprises a lubricious hydrophilic coating on an outside surface of said polymeric tubular shaft comprising a polyacrylic acid hydrophilic polymer.

29. The stent of claim 23, wherein the stent further comprises a radio-opacifying agent comprising bismuth subcarbonate, and the stent further comprises a lubricious hydrophilic coating on an outside surface of said polymeric tubular shaft comprising a polyacrylic acid hydrophilic polymer.

30. The stent of claim 1, wherein said matrix polymer comprises an ethylene vinyl acetate copolymer, the microbial attachment/biofilm synthesis inhibitor comprises a non-steroidal anti-inflammatory drug comprising ketorolac or a salt or derivative thereof, and the stent further comprises a radio-opacifying agent comprising bismuth subcarbonate, and the stent further comprises a lubricious hydrophilic coating on an outside surface of said polymeric tubular shaft.

31. The stent of claim 1, wherein the antimicrobial species comprises triclosan or chlorhexidine.

32. The stent of claim 30, wherein the antimicrobial species comprises triclosan or chlorhexidine.

* * * * *